(12) United States Patent
Panzner et al.

(10) Patent No.: US 9,066,867 B2
(45) Date of Patent: Jun. 30, 2015

(54) AMPHOTERIC LIPOSOMES

(75) Inventors: Steffen Panzner, Halle (DE); Yvonne Kerwitz, Nordhausen (DE); Una Rauchhaus, Halle (DE); Silke Lutz, Halle (DE); Gerold Endert, Halle (DE)

(73) Assignee: Marina Biotech, Inc., Bothell, WA (US)

( * ) Notice: Subject to any disclaimer, the term of this patent is extended or adjusted under 35 U.S.C. 154(b) by 895 days.

(21) Appl. No.: 12/807,707

(22) Filed: Sep. 9, 2010

(65) Prior Publication Data

US 2011/0076322 A1 Mar. 31, 2011

Related U.S. Application Data

(63) Continuation of application No. 11/521,857, filed on Sep. 15, 2006, now abandoned.

(60) Provisional application No. 60/717,199, filed on Sep. 15, 2005, provisional application No. 60/717,291, filed on Sep. 15, 2005, provisional application No. 60/717,293, filed on Sep. 15, 2005.

(30) Foreign Application Priority Data

| Sep. 15, 2005 | (EP) | .................................... | 05020216 |
| Sep. 15, 2005 | (EP) | .................................... | 05020217 |
| Sep. 15, 2005 | (EP) | .................................... | 05020218 |
| Nov. 4, 2005 | (WO) | ................. | PCT/EP2005/011905 |
| Nov. 4, 2005 | (WO) | ................. | PCT/EP2005/011908 |
| Nov. 21, 2005 | (EP) | .................................... | 05090322 |
| May 10, 2006 | (EP) | .................................... | 06113784 |

(51) Int. Cl.
*A61K 48/00* (2006.01)
*A61K 9/127* (2006.01)
*A61K 9/00* (2006.01)
*C12N 15/88* (2006.01)

(52) U.S. Cl.
CPC ............. *A61K 9/1271* (2013.01); *A61K 9/0019* (2013.01); *A61K 48/00* (2013.01); *C12N 15/88* (2013.01)

(58) Field of Classification Search
USPC ........................................................ 424/450
See application file for complete search history.

(56) References Cited

U.S. PATENT DOCUMENTS

| 5,296,231 | A | 3/1994 | Yarosh | 424/450 |
| 5,834,012 | A | 11/1998 | Perez-Soler et al. | 424/450 |
| 6,197,584 | B1 | 3/2001 | Bennett et al. | 435/366 |
| 6,287,591 | B1 | 9/2001 | Semple et al. | 424/450 |
| 2003/0099697 | A1 | 5/2003 | Panzner et al. | 424/450 |
| 2004/0037874 | A1 | 2/2004 | Hong et al. | 424/450 |
| 2004/0186071 | A1 | 9/2004 | Bennett et al. | 514/44 A |
| 2005/0064595 | A1* | 3/2005 | MacLachlan et al. | 435/458 |
| 2006/0159737 | A1 | 7/2006 | Panzner et al. | 424/450 |
| 2006/0216343 | A1 | 9/2006 | Panzner et al. | 424/450 |
| 2007/0104775 | A1 | 5/2007 | Panzner et al. | 424/450 |

FOREIGN PATENT DOCUMENTS

| EP | 0 795 325 | 9/1997 |
| EP | 1 392 341 | 6/2002 |
| EP | 1 764 090 | 9/2005 |
| EP | 1 658 839 | 11/2005 |
| EP | 1 764 089 | 3/2007 |
| WO | WO 98/21322 | 5/1998 |
| WO | WO 98/49350 | 11/1998 |
| WO | WO 99/32619 | 7/1999 |
| WO | WO 00/21370 | 4/2000 |
| WO | WO 00/59474 | 10/2000 |
| WO | WO 02/055693 | 7/2002 |
| WO | WO 02/066012 | 8/2002 |
| WO | WO 02/066013 | 8/2002 |
| WO | WO 02/066489 | 8/2002 |
| WO | WO 02/066490 | 8/2002 |
| WO | WO 03/070220 | 8/2003 |
| WO | WO 03/070735 | 8/2003 |
| WO | WO 2004/053118 | 6/2004 |
| WO | WO 2004/090108 | 10/2004 |
| WO | WO 2006/048329 | 5/2006 |
| WO | WO 2006/053646 | 5/2006 |
| WO | WO 2007/031333 | 3/2007 |

OTHER PUBLICATIONS

Alderson et al, J. Exp. Med. 178:669-674, 1993.*
Baccam, Membrane-bound CD154, but not CD40-specific antibody, mediates NF-xB-independent IL-6 production in B cells, Eur. J. Immunol. 1999.29:3855-3866.
Budker, pH-sensitive, cationic liposomes: A new synthetic virus-like vector, Nature Biotechnology vol. 14 June 1996, pp. 760-764.
Cho-Chung, Oligonucleotides as transcription factor decoys, Current Opinion in Molecular Therapeutics 1999, vol. 1 (3):386-382.
Crooke, Molecular mechanisms of action of antisense drugs, Biochimica et Biophysica Acta 1489 (1999) 31-44.
Dass, Cytotoxicity issues pertinent to lipoplex-mediated gene therapy in-vivo, Journal of Pharmacy and Pharmacology, 2002, 54: 593-601.
Filion, Toxicity and immunomodulatory activity of liposomal vectors formulated with cationic lipids toward immune effector cells, Biochimica et Biophysica Acta 1329 (1997) 345-356.
Fiset, Antisense Oligonucleotides: problems with use and solutions, Reviews in Biology and Biotechnology, vol. 1, No. 2, May 2001, pp. 27-33.

(Continued)

*Primary Examiner* — Kevin Hill
(74) *Attorney, Agent, or Firm* — Eckman Basu LLP

(57) ABSTRACT

A serum-stable mixture of lipids capable of encapsulating an active agent to form a liposome, said mixture comprising phosphatidylcholine and phosphatidylethanolamine in a ratio in the range of about 0.5 to about 8. The mixture may also include pH sensitive anionic and cationic amphiphiles, such that the mixture is amphoteric, being negatively charged or neutral at pH 7.4 and positively charged at pH 4. Amphoteric liposomes comprising such a mixture may be used for encapsulating nucleic acid therapeutics, such as oligonucleotides and DNA plasmids. The drug/lipid ratio may be adjusted to target the liposomes to particular organs or other sites in the body.

14 Claims, 6 Drawing Sheets

(56) References Cited

OTHER PUBLICATIONS

Gao Dingcheng, On the pathophysiological significance of CD154/CD40-mediated leukocyte-endothelial cell interaction, Dissertation, Georg-August-Universitat zu Gottingen, Goettingen 2003, pp. 1-69.

Gruss, CD40/CD40 Ligand Interactions in Normal, Reactive and Malignant Lympho-Hematopoietic Tissues, Leukemia and Lymphoma, vol. 24, pp. 393-422, 1997 (Overseas Publishers Association) Amsterdam.

Guidance for Industry, Draft Version of Liposome Drug Products, Chemistry, Manufacturing, and Controls; Human Pharmacokinetics and Bioavailability; and Labeling Documentation, prepared by the Liposome Working Group of the Complex Drug Substances Coordinating Committee (CDSCC) in the Center for Drug Evaluation and Research (COER) at the FDA, dated Jul. 29, 2002, pp. 1-12.

Hirko, Cationic Lipid Vectors for Plasmid DNA Delivery, Current Medicinal Chemistry, 2003, 10, 1185-1193.

Hostager, Recruitment of CD40 and Tumor Necrosis Factor Receptor-associated Factors 2 and 3 to Membrane Microdomains during CD40 Signaling, The Journal of Biological Chemistry, vol. 276, No. 20, Issue of May 19, pp. 16392-16398, 2000.

Klimuk, Enhanced Anti-Inflammatory Activity of a Liposomal Intercellular Adhesion Molecule-1 Antisense Oligodeoxynucleotide in an Acute-Model of Contact Hypersensitivity, The Journal of Pharmacology and Experimental Therapeutics, vol. 292:480-488, 2000.

Mann, Therapeutic applications of transcription factor decoy oligonucleotides, The Journal of Clinical Investigation, Nov. 2000, vol. 106, No. 9, pp. 1071-1075.

Maurer, Lipid based systems for the intracellular delivery of genetic drugs, Molecular Membrane Biology, 1999, 16, 129-140.

Meidan, Interaction of oligonucleotides with cationic lipids: the relationship between electrostatics, hydration and state of aggregation, Biochimica et Biophysica Acta 1464 (2000) 251-261.

Mocali, Increased plasma levels of soluble CD40, together with the decrease of TGFJ31, as possible differential markers of Alzheimer disease, Experimental Gerontology 39 (2004) 1555-1561.

Morrissey, Potent and persistent in vivo anti-HBV activity of chemically modified siRNAs, Nature Biotechnology, Letters, vol. 23 No. 8 August 2005, Published online Jul. 24, 2005.

Paulie, Monoclonal antibodies to antigens associated with transitional cell carcinoma of the human urinary bladder, Cancer Immunol Immunother (1984) 17:173-179.

Pluvinet, RNAi-mediated silencing of CD40 prevents leukocyte adhesion on CD154-activated endothelial cells, Blood, Dec. 1, 2004, vol. 104, No. 12, pp. 3642-3646.

Richardson, Gene Repair and Transposon-Mediated Gene Therapy, Stem Cells 2002;20:105-118.

Rushworth, Inhibition of CD40 Mediated Endothelial Cell Activation with Antisense Oligonucleotides, Transplantation, vol. 78, 635-642, No. 4, Feb. 27, 2002.

Semple, Efficient encapsulation of antisense oligonucleotides in lipid vesicles using ionizable aminolipids: formation of novel small multilamellar vesicle structures, Biochimica et Biophysica Acta 1510 (2001) 152-166.

Song, Characterization of the inhibitory effect of PEG-lipid conjugates on the intracellular delivery of plasmid and antisense DNA mediated by cationic lipid liposomes, Biochimica et Biophysica Acta 1558 (2002) 1-13.

Tijsterman, Dicers at RISC: The Mechanism of RNAi, Cell, vol. 117, 1-4, Apr. 2, 2004, Cell Press.

Hafez, On the mechanism whereby cationic lipids promote intracellular delivery of polynucleic acids, Gene Therapy (2001) B, 1188-1196.

Stamatatos, Interactions of Cationic Lipid Vesicles with Negatively Charged Phospholipid Vesicles and Biological Membranes, Biochemistry 1988, 27, 3917-3925.

Wrobel, Fusion of cationic liposomes with mammalian cells occurs after endocytosis, Biochimica ct Biophysica Acta 1235 (1995) 296-304.

* cited by examiner animal 94
front right paw is arthritic front left   2142
front right  8907
back left    2785
back right   2829 animal 71
back right paw is arthritic front left   1719
front right  1865
back left    2176
back right   7016 healthy animal without Cy5.5 front left   2404
front right  3794
back left    2709
back right   3258

FIG. 10 gcctcgcgccATGGTTCGTCTGCCCTCTGAAGTGTCTCCTCTGGGGCTGCTTTTTGACCGCCGTCCACCCAGAACCACCCACTTCATGCAAGAAAACCAATAC
        ASO 1

CCAACAAAACAGCCGGTGCTGTAATTTGTGCCCCGCCAGGACAGAGAAACTGGTGAACCACTGCACAGAGGTCACTGAAACAGAATGCCTTCCTTGCAGTTCCA
                                                              ASO 2

GCGAATTCCTAGCCACCTGGAATAGAGAAACACTGTCATCAGCACAAATACTGCGACCCCCAACCTAGGTCTCCAGTTCCAGAGGAGGGCACCTCGAA
                                              ASO 3

AACAGACACCACTTGTGTGCAGTGAAGGCCATCACTGTACCACAACAGCGCCTGTGAAAGTTGCACCTTGCACAAGCTTGTGCTTCCCTGGCCTCGGGGTC
                                                                                     ASO 4

AAGCAGATGGCGACAGAGGTTTCTGACACTATCTGTGAACCCTGCCCAGTTGGGCTTCTCTCCAATGTATCATCTGCTTCAGAAAAGTGTCAGCCTTGGA
CAAGCTGCGAGAGCAAAGGCCTGGTGGAACAAGTGCGGGACTAACAAGACCGATGTGTCTGGTTTCCAGAGTCGGATGAGAGCCCTGGTGTTAT
ASO 5

CCCCATCACGCTGGGGATCCTCGTGTTTGCCGTCCTGTTCTCTGTATCAGAAAGGTGACCAAGGAGCAGGAGACTAAGGCCCTGCACCCTAAGACT
                                                                         ASO 6

GAAAGGCAGGATCCCGTGAGAGACGATTGATCTGGAGGATTTTCCCGACTCCACCGCTCCGGTGCAGGAGACCTTACATTGGTGCCAGCCCGTCACCCAGG
                     ASO 7

AGGATGGCAAAGAGAGCCGCATCTCCGTGCAGGAGCGAGAGTGAggctgtgcgtggcaggagcgtggaggcacggtggagcatgtgactggagag
                                                       ASO 8 cccggggcggctgctgctgtgcggtggtgagagggtggtgctgggcacagcccctctgcctgcaccctgcagtccagatacagtccacctcgag
                                                                                                     ASO 9 gagcttctcaccccagccctggagccattcaatctcagtttgcttttcccgatggagacaaactttgggagtcacagccacagtaataaccaccagag cttccaaccagaggttcagtacctgcagatgcaaggatggcgtctaggagcccaggaggcatatacatgacttccaacactgcattgttcgtgacag
                                                                                            ASO 10 tgagtgactggaaactgcttaactgtccatcaacagggactggctaaataaattgtaacatgtttatgcaaaaaaaaa

SEQUENCE LISTING

<160> NUMBER OF SEQ ID NOS: 87

<210> SEQ ID NO 1
<211> LENGTH: 1004
<212> TYPE: DNA
<213> ORGANISM: Homo sapiens

<400> SEQUENCE: 1

```
gcctcgctcg ggcgcccagt ggtcctgccg cctggtctca cctcgccatg gttcgtctgc     60
ctctgcagtg cgtcctctgg ggctgcttgc tgaccgctgt ccatccagaa ccacccactg    120
catgcagaga aaaacagtac ctaataaaca gtcagtgctg ttctttgtgc cagccaggac    180
agaaactggt gagtgactgc acagagttca ctgaaacgga atgccttcct tgcggtgaaa    240
gcgaattcct agacacctgg aacagagaga cacactgcca ccagcacaaa tactgcgacc    300
ccaacctagg gcttcgggtc cagcagaagg gcacctcaga aacagacacc atctgcacct    360
gtgaagaagg ctggcactgt acgagtgagg cctgtgagag ctgtgtcctg caccgctcat    420
gctcgcccgg ctttggggtc aagcagattg ctacaggggt ttctgatacc atctgcgagc    480
cctgcccagt cggcttcttc tccaatgtgt catctgcttt cgaaaaatgt caccctgga    540 caagctgtga gaccaaagac ctggttgtgc aacaggcagg cacaaacaag actgatgttg    600
tctgtggtcc ccaggatcgg ctgagagccc tggtggtgat ccccatcatc ttcgggatcc    660
tgtttgccat cctcttggtg ctggtcttta tcaaaaaggt ggccaagaag ccaaccaata    720
aggcccccca ccccaagcag gaaccccagg agatcaattt tcccgacgat cttcctggct    780
ccaacactgc tgctccagtg caggagactt tacatggatg ccaaccggtc acccaggagg    840
atggcaaaga gagtcgcatc tcagtgcagg agagacagtg aggctgcacc cacccaggag    900
tgtggccacg tgggcaaaca ggcagttggc cagagagcct ggtgctgctg ctgcaggggt    960
```

```
gcaggcagaa gcggggagct atgcccagtc agtgccagcc cctc                1004
```

<210> SEQ ID NO 2
<211> LENGTH: 938
<212> TYPE: DNA
<213> ORGANISM: Mus musculus

<400> SEQUENCE: 2

```
gcctcctggc ccttcagctg tggtctttcc cgttttctga ctttgcggtg acactgggga    60
cttccttaga cctctctgga gacgctttcg gttctgcaga gattcccagg ggtattgtgg   120
gtggggtggg gtaacaatag tgtccctgtg gcgctcccag tccctatagt aatccttcac   180
ccctctgcta tcttgcaatc aggagagtcc ttagccctgc tataggtggc ttttgaggtc   240
ctggatgcga ggaggggggac tggggggtgg gtcgggtaat gtaagaaaag ggctccttttt  300
gggaccctgg ctcctccagc caccttggtg cccatccctt aaactcttgg ggacaatcag   360
actcctggga aggtcctggg gaaatccctg ctcagtgact agccataggc ccaccgcgat   420
tggtgcccga agaccccgcc ctcttcctgg gcgggactcc tagcagggac tttggagtga   480
cttgtggctt cagcaggagc cctgtgattt ggctcttctg atctcgccct gcgatggtgt   540
ctttgcctcg gctgtgcgcg ctatggggct gcttgttgac agcggtgagt ggcttgtgtt   600
ctaacctcca agggagttag ggcttagaga gtgagagatg gaaagaggaa agaggagaca   660
agactttgga gatgagagat cttcctactg gaagcggcgg ttagtaggat gggcaagatc   720
tctcgcgtct tgacacacac acacacacac acaaatgagg tgggctgctc ctctttcctt   780
ccagaaggtc ggggttctgt tccacgaagc ccacagggaa ccttagggag ggcattcctc   840
cacagcggtg cctggacagc tttgtctgac ccaagccttg ctccggagct gactgcagag   900
actggaaagg gttagcagac aggaagcctg gctgggggg                          938
```

<210> SEQ ID NO 3
<211> LENGTH: 547
<212> TYPE: DNA
<213> ORGANISM: Rattus sp.
<220> FEATURE:
<221> NAME/KEY: modified_base
<222> LOCATION: (334)
<223> OTHER INFORMATION: a, c, g, t, unknown or other

<400> SEQUENCE: 3

```
tgggacccct gtgatctggc tgctctgatc tcgctctgca atgctgcctt tgcctcagct    60
gtgcgcgctc tggggctgct tgttgacagc ggtccatcta ggacagtgtg ttacgtgcag   120
tgacaaacag tacctccaag gtggcgagtg ctgcgatttg tgccagccgg gaaaccgact   180
agttagccac tgcacagctc ttgagaagac ccaatgccaa ccgtgcgact caggcgaatt   240
ctcagctcac tggaacaggg agatccgctg ccaccagcac cgacactgcg aactcaatca   300
agggcttcag gttaagaagg agggcaccgc ggtntcagac actgttttgta cctgcaagga   360
agggcagcac tgcgccagca aggagtgcga gacgtgcgct cagcacaggc cctgtggccc   420
tggctttgga gtcgtgcaga tggccactga gactactgat accgtctgcc aaccctgccc   480
ggtcggattc ttctccaatg ggtcatcact tttgaaaag tgtcatccat ggacaagctg   540
tgaagat                                                             547
```

<210> SEQ ID NO 4
<211> LENGTH: 1284
<212> TYPE: DNA

<213> ORGANISM: Sus sp.

<400> SEQUENCE: 4

```
gcctcgccat ggttcgtctg cctctgaagt gtctcctctg gggctgcttt ttgaccgccg      60
tccacccaga accacccact tcatgcaaag aaaaccaata cccaacaaac agccggtgct     120
gtaatttgtg cccgccagga cagaaactgg tgaaccactg cacagaggtc actgaaacag     180
aatgccttcc ttgcagttcc agcgaattcc tagccacctg aatagagag aaacactgtc     240
atcagcacaa atactgcgac cccaacctag gtctccaggt ccagagggag ggcacctcga     300
aaacagacac cacttgtgtg tgcagtgaag gccatcactg taccaacagc gcctgtgaaa     360
gttgcacctt gcacagcttg tgcttccctg gcctcggggt caagcagatg gcgacagagg     420
tttctgacac tatctgtgaa ccctgcccag ttggcttctt ctccaatgta tcatctgctt     480
cagaaaagtg tcagccttgg acaagctgcg agagcaaagg cctggtggaa caacgtgcgg     540
ggactaacaa gaccgatgtt gtctgtggtt tccagagtcg gatgagagcc ctggtggtta     600
tccccatcac gctgggatc ctgtttgccg tcctgttggt atttctctgt atcagaaagg     660
tgaccaagga gcaggagact aaggccctgc accctaagac tgaaaggcag gatcccgtgg     720
agacgattga tctggaggat tttcccgact ccaccgctcc ggtgcaggag accttacatt     780
ggtgccagcc cgtcacccag gaggatggca agagagccg catctccgtg caggagcgag     840
agtgaggctg tgcgtggcca ggagcgtgga ggcacgggca caggggcatg tgactggaga     900
gcccggggcg gctgctgctg ctgtggcggt ggtgagaggg tggtgctggg cacagcccct     960
tctgcctgca cccctgcagt ccagatacag tccacctcga ggagcttctc accccagccc    1020
tggagcccat tcaatctcag tttgctttta aagatggaga caaaactttg gggagtcaca    1080
gccacagtaa taaccaccag agcttccaac ccagaggttc agtacctgca gatgcaaggg    1140
atggcgtcta ggagcccagg aggcatatac atgactgtcc accactgcat tgttcgtgac    1200
agtgagtgac tggaaactgc ttaactgtcc atcaacaggg gactggctaa ataaaattgt    1260
aacatgttta tgcaaaaaaa aaaa                                           1284
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5

```
ccaggcggca ggaccact                                                    18
```

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6

```
gaccaggcgg caggacca                                                    18
```

<210> SEQ ID NO 7
<211> LENGTH: 18
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 7
aggtgagacc aggcggca                                                   18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcagaggcag acgaacca                                                   18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcaagcagcc ccagagga                                                   18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggtcagcaag cagcccca                                                   18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gacagcggtc agcaagca                                                   18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gatggacagc ggtcagca                                                   18

<210> SEQ ID NO 13
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 13
tctggatgga cagcggtc                                                    18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggtggttctg gatggaca                                                    18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gtgggtggtt ctggatgg                                                    18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcagtgggtg gttctgga                                                    18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctggcacaaa gaacagca                                                    18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtgcagtcac tcaccagt                                                    18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 19
attccgtttc agtgaact                                                 18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttcaccgcaa ggaaggca                                                 18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctctgttcca ggtgtcta                                                 18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ctggtggcag tgtgtctc                                                 18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggtgcccttc tgctggac                                                 18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctgaggtgcc cttctgct                                                 18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gtgtctgttt ctgaggtg					18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
acaggtgcag atggtgtc					18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtgccagcct tcttcaca					18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tgcaggacac agctctca					18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gagcggtgca ggacacag					18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aatctgcttg accccaaa					18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gctcgcagat ggtatcag                                              18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcagggctcg cagatggt                                              18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gactgggcag ggctcgca                                              18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gcagatgaca cattggag                                              18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tcgaaagcag atgacaca                                              18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gtccaagggt gacatttt                                              18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
caggtctttg gtctcaca                                        18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ctgttgcaca accaggtc                                        18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gtttgtgcct gcctgttg                                        18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gtcttgtttg tgcctgcc                                        18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
caccaccagg gctctcag                                        18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gggatcacca ccagggct                                        18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
gtcgggaaaa ttgatctc                                                       18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ggagccagga agatcgtc                                                       18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tggagccagg aagatcgt                                                       18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tggcatccat gtaaagtc                                                       18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ggtgcagcct cactgtct                                                       18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aactgcctgt ttgcccac                                                       18

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sequence

<400> SEQUENCE: 49
gcgaauuccu agacaccugu u                                                   21
```

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
    siRNA sequence

<400> SEQUENCE: 50
cuggugagug acugcacagu u                                              21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
    siRNA sequence

<400> SEQUENCE: 51
uacugcgacc ccaaccuagu u                                              21

<210> SEQ ID NO 52
<211> LENGTH: 14
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 52
agacaccatc gcag                                                      14

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 53
gcgagatcag aagag                                                     15

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 54
cgctgtcaac aagca                                                     15

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 55
ctgccctaga tggac                                                     15

<210> SEQ ID NO 56
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ctggctggca caaat                                                      15

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cttgtccagg gataa                                                      15

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cacagatgac attag                                                      15

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tgatatagag aaaca                                                      15

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ctcattatcc tttgg                                                      15

<210> SEQ ID NO 61
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ggttcagacc agg                                                        13

<210> SEQ ID NO 62
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tttatttagc cagta                                                      15

<210> SEQ ID NO 63
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
agccccacgc actgg                                                      15

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tctcactcct atcccagt                                                   18

<210> SEQ ID NO 65
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
attagtctga ctcgt                                                      15

<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
acattagtct gactc                                                      15

<210> SEQ ID NO 67
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cagatgacat tagtc                                                      15

<210> SEQ ID NO 68

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ctggactcac cacag                                                          15

<210> SEQ ID NO 69
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ggactcacca cagat                                                          15

<210> SEQ ID NO 70
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
actcaccaca gatga                                                          15

<210> SEQ ID NO 71
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tcaccacaga tgaca                                                          15

<210> SEQ ID NO 72
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
accacagatg acatt                                                          15

<210> SEQ ID NO 73
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
agatgacatt ag                                                             12

<210> SEQ ID NO 74
<211> LENGTH: 13
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
cagatgacat tag                                                          13

<210> SEQ ID NO 75
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
acagatgaca ttag                                                         14

<210> SEQ ID NO 76
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ccacagatga cattag                                                       16

<210> SEQ ID NO 77
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
accacagatg acattag                                                      17

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
caccacagat gacattag                                                     18

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tcaccacaga tgacattag                                                    19

<210> SEQ ID NO 80
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 80
ctcaccacag atgacattag                                                    20

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
accgctgtca acaagcagc                                                     19

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tcctagatgg accgctgt                                                      18

<210> SEQ ID NO 83
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
taacacactg tcctag                                                        16

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gctgatgaca gtgtttct                                                      18

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gcctcactct cgctcctg                                                      18

<210> SEQ ID NO 86
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 86
ggactgtatc tggactgc                                                   18

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gtggacagtc atgtatat                                                   18
```

AMPHOTERIC LIPOSOMES

CROSS-REFERENCE TO RELATED APPLICATIONS

This application is a continuation of U.S. application Ser. No. 11/521,857, filed on Sep. 15, 2006 now abandoned, which claims priority from U.S. Provisional Application Ser. No. 60/717,199, filed on Sep. 15, 2005; U.S. Provisional Application Ser. No. 60/717,291, filed on Sep. 15, 2005; U.S. Provisional Application Ser. No. 60/717,293, filed Sep. 15, 2005; European Application No. 05020218.3, filed on Sep. 15, 2005; European Application No. 05020217.5, filed on Sep. 15, 2005; European Patent Application No. 050202167.7, filed on Sep. 15, 2005; PCT Application No. PCT/EP2005/011905, filed on Nov. 4, 2005; PCT Application No. PCT/EP2005/011908, filed on Nov. 4, 2005; U.S. application Ser. No. 11/266,999, filed on Nov. 4, 2005 (abandoned); U.S. application Ser. No. 11/267,423, filed on Nov. 4, 2005 (abandoned); European Application No. 06113784.0, filed on May 10, 2006; and European Application No. 05090322.8, filed on Nov. 21, 2005. The contents of each of these applications are incorporated herein by reference in their entireties.

Each of the applications and patents cited in this text, as well as each document or reference cited in each of the applications and patents (including during the prosecution of each issued patent; "application cited documents"), and each of the U.S. and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in the practice of the invention.

FIELD OF THE INVENTION

The present invention relates to amphoteric liposomes and has particular reference to such liposomes having improved stability in human or animal serum. The present invention also comprehends mixtures of lipids capable of encapsulating active agents or ingredients such, for example, as drugs to form liposomes and pharmaceutical compositions comprising such liposomes.

BACKGROUND OF THE INVENTION

Oligonucleotides represent a novel class of drugs that can very specifically down-regulate or interfere with protein expression. Such oligonucleotides include antisense, locked nucleic acids (LNA), peptide nucleic acids (PNA), morpholino nucleic acids (Morpholinos), small interfering RNAs (siRNA) and transcription factors decoys of various chemistries. A detailed description of the different mechanisms of action of such oligonucleotide therapeutics can be found in the literature (e.g., Crooke in BBA (1999), 1489(1), 31-44; Tijsterman, et al. in Cell (2004), 117(1), 1-3; and Mann, et al. in J Clin Invest, (2000), 106(9), 1071-5).

The use of oligonucleotides for gene repair applications (see, e.g., Richardson, et al. in Stem Cells (2002), 20, 105-118) and micro RNAs are other examples from this rapidly growing field.

It is known in the art that nucleic acid therapeutics, irrespective of their actual chemical origin, may lack therapeutic efficacy owing to their instability in body fluids or because of inefficient uptake into cells, or both. Chemical modifications of such oligonucleotide, including the above-mentioned variants, as well as the formation of conjugates with ligands or polymers, represent one strategy to overcome such practical limitations.

A second set of strategies involves the use of carrier systems, in particular liposomes, for protecting, targeting and affording enhanced uptake into cells. Liposomes are artificial single, oligo or multilamellar vesicles having an aqueous core and being formed from amphiphilic molecules having both hydrophobic and hydrophilic components (amphiphiles). The cargo may be trapped in the core of the liposome, disposed in the membrane layer or at the membrane surface. Such carrier systems should meet an optimum score of the following criteria: high encapsulation efficiency and economical manufacture, colloidal stability, enhanced uptake into cells and of course low toxicity and immunogenicity.

Anionic or neutral liposomes are often excellent in terms of colloidal stability, as no aggregation occurs between the carrier and the environment. Consequently their biodistribution is excellent and the potential for irritation and cytotoxicity is low. However, such carriers lack encapsulation efficiency and do not provide an endosomolytic signal that facilitates further uptake into cells (Journal of Pharmacology and Experimental Therapeutics (2000), 292, 480-488 by Klimuk, et al.).

A great many of publications deal with cationic liposomal systems; see, e.g., Molecular Membrane Biology (1999), 16, 129-140 by Maurer, et al.; BBA (2000) 1464, 251-261 by Meidan, et al.; Reviews in Biology and Biotechnology (2001), 1(2), 27-33 by Fiset & Gounni. Although cationic systems provide high loading efficiencies, they lack colloidal stability, in particular after contact with body fluids. Ionic interactions with proteins and/or other biopolymers lead to in situ aggregate formation with the extracellular matrix or with cell surfaces. Cationic lipids have often been found to be toxic as shown by Filion, et al. in BBA (1997), 1329(2), 345-356; Dass in J. Pharm. Pharmacal. (2002), 54(5), 593-601; Hirko, et al. in Curr. Med. Chem., 10(14), 1185-1193.

These limitations were overcome by the addition of components that provide a steric stabilisation to the carriers. Polyethylenglycols of various chain length, for example, are known to eliminate aggregation problems associated with the use of cationic components in body fluids, and PEGylated cationic liposomes show enhanced circulation times in vivo (BBA (2001) 1510, 152-166 by Semple, et al.). However, the use of PEG does not solve the intrinsic toxicity problems associated with cationic lipids. It is also known that PEG substantially inhibits the productive entry of such liposomes into the cells or their intracellular delivery (Song, et al. in BBA (2002), 1558(1), 1-13). Quite recently, Morrissey, et al. (Nature Biotechnology (2005), 23 (8), 1002-1007) described a diffusible PEG-lipid for a cationic vector that is able to transfer siRNA into liver cells in vivo. However, the huge demand for such solutions and the given attrition rate of clinical development more than motivates the development of conceptually independent solutions.

Amphoteric liposomes represent a recently described class of liposomes having an anionic or neutral charge at pH 7.5 and a cationic charge at pH 4. WO 02/066490, WO 02/066012 and WO 03/070735, all to Panzner, et al. and incorporated herein by reference, give a detailed description of amphoteric liposomes and suitable lipids therefor. Further disclosures are made in WO 03/070220 and WO 03/070735, also to Panzner, et al. and incorporated herein by reference, which describe further pH sensitive lipids for the manufacture of such amphoteric liposomes.

Amphoteric liposomes have an excellent biodistribution and are very well tolerated in animals. They can encapsulate nucleic acid molecules with high efficiency.

The use of amphoteric liposomes as carriers for drugs for the prevention or treatment of different conditions or diseases in mammals requires stability of the liposomes after their injection into the bloodstream. For systemic applications especially, the drug must be stably encapsulated in the liposomes until eventual uptake in the target tissue or cells. The FDA's guidelines prescribe specific preclinical tests for drugs comprising liposomal formulations. For example, the ratio of encapsulated drug to free drug must be determined during the circulation time in the bloodstream.

After the injection of liposomes into the bloodstream, serum components interact with the liposomes and may lead to permeabilisation of the liposomal membrane. However, the release of a drug that is encapsulated by the liposome also depends upon the molecular dimensions of the drug. This means that a plasmid drug with a size of thousands of base pairs, for example, may be released much more slowly than smaller oligonucleotides or other small molecules. For liposomal delivery of drugs it is essential that the release of the drug during the circulation of the liposomes is as low as possible.

OBJECTS OF THE INVENTION

An object of the present invention therefore is to provide liposomes and mixtures of lipids capable of forming such liposomes having improved stability upon contact with human or animal serum.

In particular, an object of the present invention is to provide amphoteric liposomes having such improved serum stability.

Another object of the invention is to provide pharmaceutical compositions comprising such liposomes as a carrier for the targeted delivery of active agents or ingredients, including drugs such as nucleic acid drugs, e.g., oligonucleotides and plasmids.

A particular object of the present invention is to provide such a pharmaceutical composition for the treatment or prophylaxis of inflammatory, immune or autoimmune disorders of humans or non-human animals.

Yet another object of the present invention is to provide methods for the treatment of human or non-human animals in which a pharmaceutical composition comprising an active agent is targeted to a specific organ or organs, tumours or sites of infection or inflammation.

SUMMARY OF THE INVENTION

According to one aspect of the present invention therefore there is provided a mixture of lipids capable of encapsulating an active agent to form a liposome, said mixture comprising phosphatidylcholine (PC) and phosphatidylethanolamine (PE) in a ratio of phosphatidylethanolamine to phosphatidylcholine in the range of about 0.5 to about 8.

Suitably, said ratio range from about 0.75 to about 5, preferably from about 1 to about 4.

In some embodiments, said phosphatidylcholine may be selected from DMPC, DPPC, DSPC, POPC or DOPC, or from phosphatidylcholines from natural sources such as, for example, soy bean PC and egg PC.

Said phosphatidylethanolamines may be selected from DOPE, DMPE and DPPE.

Preferred neutral lipids include DOPE, POPC, soy bean PC and egg PC.

It is known that cholesterol may stabilise phosphatidylcholine bilayers against serum attack. However, neither POPC nor DOPE form serum stable structures by themselves. It has now been found surprisingly that mixtures of DOPE and POPC may form serum stable liposomes.

Accordingly, in a particular aspect of the present invention, said mixture of lipids may be neutral. In some embodiments said mixture may consist or consist essentially of phosphatidylcholine and phosphatidylethanolamine in a ratio in the aforementioned range.

In another aspect of the present invention there are provided neutral liposomes comprising a mixture of lipids in accordance with the invention. Such liposomes may be used as a serum-stable excipient or carrier for active agents such as drugs.

In a different aspect of the present invention however, said mixture may further comprise one or more charged amphiphiles.

Preferably said one or more charged amphiphiles are amphoteric, being negatively charged or neutral at pH 7.4 and positively charged at pH 4.

By "amphoteric" herein is meant a substance, a mixture of substances or a supra-molecular complex (e.g., a liposome) comprising charged groups of both anionic and cationic character wherein:

(i) at least one of the charged groups has a pK between 4 and 8,
(ii) the cationic charge prevails at pH 4, and
(iii) the anionic charge prevails at pH 8, resulting in an isoelectric point of neutral net charge between pH 4 and pH 8. Amphoteric character is by this definition different from zwitterionic character, as zwitterions do not have a pK in the range mentioned above. In consequence, zwitterions are essentially neutrally charged over a range of pH values; phosphatidylcholines and phosphatidylethanolamines are neutral lipids with zwitterionic character.

Suitably therefore, said mixture may comprise a plurality of charged amphiphiles which in combination with one another have amphoteric character. Preferably said one or more charged amphiphiles comprise a pH sensitive anionic lipid and a pH sensitive cationic lipid. Herein, such a combination of a chargeable cation and chargeable anion is referred to as an "amphoteric II" lipid pair. Said chargeable cation may have a pK value of between about 4 and about 8, preferably between about 5.0 or 5.5 and about 7.0 or 7.5. Said chargeable anion may have a pK value of between about 3.5 and about 7, preferably between about 4 or 4.5 and about 6.0 or 6.5. Examples include MoChol/CHEMS, DPIM/CHEMS and DPIM/DGSucc.

An "amphoteric I" lipid pair comprises a stable cation (e.g., DDAB/CHEMS, DOTAP/CHEMS and DOTAP/DOPS) and a chargeable anion, while an "amphoteric III" lipid pair comprises a stable anion and a chargeable cation (e.g., MoChol/DOPG and MoChol/Chol-SO$_4$).

It is of course possible within the scope of the present invention to use amphiphiles with multiple charges, such as, for example, amphipathic dicarboxylic acids, phosphatidic acid, amphipathic piperazine derivatives and the like. Such multi-charged amphiphiles may be pH sensitive amphiphiles or stable anions or cations, or they may have "mixed" character.

Suitably, said anionic lipid may be selected from DOGSucc, POGSucc, DMGSucc, DPGSucc and CHEMS.

Said cationic lipid may be selected from MoChol, HisChol and CHIM.

In yet another aspect of the present invention there are provided amphoteric liposomes comprising phosphatidylcholine and phosphatidylethanolamine in a ratio in the aforementioned range, a pH sensitive anionic lipid and a pH sensitive cationic lipid.

Said amphoteric liposomes may be negatively or neutrally charged at pH 7.4 and cationic at pH 4.

In another particular aspect of the present invention, said liposomes encapsulate at least one active agent. Said active agent may comprise a drug. In some embodiments said active agent may comprises a nucleic acid such as, for example, an oligonucleotide or DNA plasmid that is capable of being transcribed in a vertebrate cell into one or more RNAs, said RNAs being mRNAs, shRNAs, miRNAs or ribozymes, said mRNAs coding for one or more proteins or polypeptides.

Said oligonucleotide or other nucleic acid based drug may be encapsulated in said amphoteric liposomes. A substantial portion or all of said oligonucleotides may be physically entrapped in the amphoteric liposomes. The serum stable amphoteric liposomal formulations can be used for the intracellular delivery of drugs or for the prevention or treatment of a condition and/or disease in mammals or part of mammals, especially humans or their organs.

In some embodiments, said oligonucleotide may be adapted to target a nucleic acid encoding CD40, thereby to modulate expression of CD40 in mammalian cells. Suitably, said oligonucleotide may be directed against the mRNA of CD40.

In yet another aspect of the present invention there is provided a pharmaceutical composition comprising active agent-loaded amphoteric liposomes in accordance with the present invention and a pharmaceutically acceptable vehicle therefor.

Said composition may be formulated for high or low lipid doses, and suitably therefore the drug/lipid ratio may be adjusted to a desired lipid concentration. In some embodiments, said composition may further comprise empty liposomes to decrease said drug/lipid ratio, said empty liposomes having the same or similar size and composition to said active agent loaded liposomes. Said empty liposomes may comprise a mixture of lipids according to the present invention.

In yet another aspect, the present invention comprehends the use of a pharmaceutical composition according to the present invention for the prevention or treatment of an inflammatory, immune or autoimmune disorder of a human or non-human animal, wherein said composition comprises an oligonucleotide adapted to target a nucleic acid encoding CD40 for modulating the expression of CD40 in mammalian cells.

Said composition may be formulated for systemic or local administration. When used systemically, the present invention comprises the use of said composition inter alia for the prevention or treatment of graft rejection, graft-versus-host disease, diabetes type I, multiple sclerosis, systemic lupus erythematosus, rheumatoid arthritis, asthma, inflammatory bowel disease, psoriasis or thyroiditis.

When formulated for local application, the invention comprises the use of said composition inter alia for the prevention or treatment of graft rejection, graft-versus-host disease, inflammatory bowel disease, asthma, Crohn's disease or ulcerative colitis.

These and other embodiments are disclosed or are obvious from and encompassed by the following Detailed Description.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which:

FIG. 10 is a porcine CD40 cDNA sequence (SEQ ID NO:4) for targeting in accordance with the present invention.

DETAILED DESCRIPTION OF THE INVENTION

Figure 1:
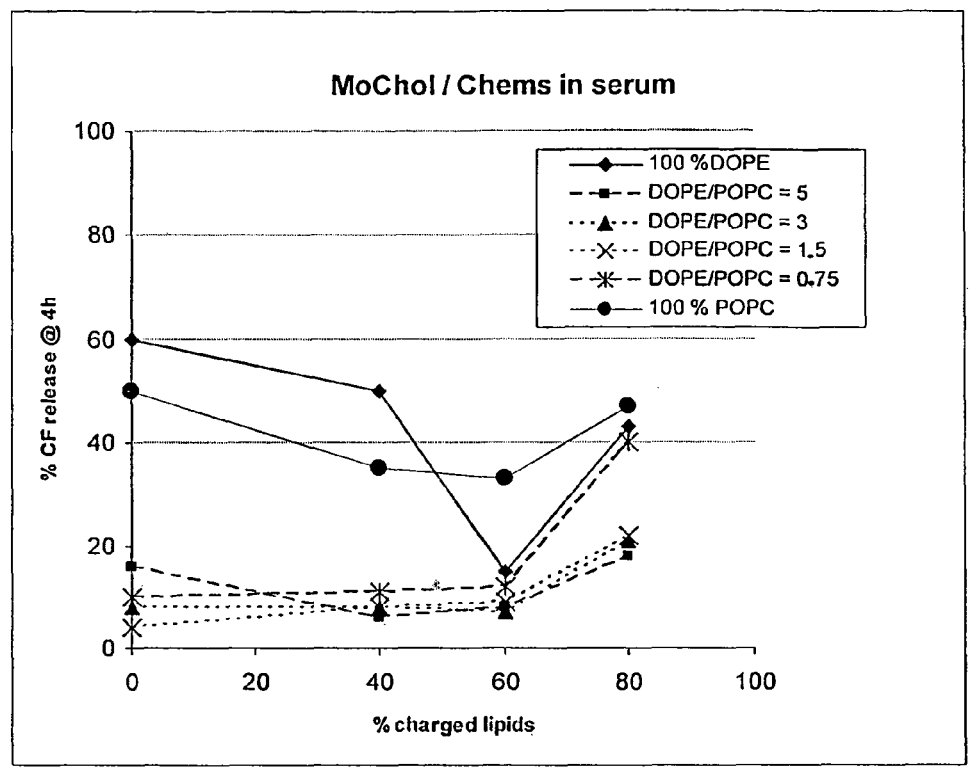
FIG. 1 is a graph of carboxyfluorescein (CF) release from the MoChol/CHEMS formulations of Table 1 (i.e., formulations comprising 100% DOPE (no POPC), DOPE/POPC ratios of 5, 3, 1.5, and 0.75, and 100% POPC (no DOPE)) below after incubation in full human serum for 4 hours. CF release is expressed as % of the unquenched CF signal. The x-axis shows the total amount of charged lipid at a 1:1 ratio between MoChol and CHEMS.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

As mentioned above, the amphoteric liposomes of the present invention may comprise anionic and cationic components, wherein both components are pH-sensitive, as disclosed in WO 02/066012, the contents of which are incorporated herein by reference.

Cationic lipids that are sensitive to pH are disclosed in WO 02/066489 and WO 03/070220, and in the references made therein, in particular Budker, et al. 1996, Nat Biotechnol. 14(6):760-4, the contents of all of which are incorporated herein by reference.

Preferred cationic components are MoChol, HisChol and CHIM, especially MoChol.

Preferred anionic lipids are selected from the group comprising: DOGSucc, POGSucc, DMGSucc, DPGSucc and CHEMS, especially DOGSucc, DMGSucc and CHEMS.

The following abbreviations for lipids are used herein, the majority of which abbreviations are in standard use in the literature:

PC Phosphatidylcholine, unspecified membrane anchor
PE Phosphatidylethanolamine, unspecified membrane anchor
DMPC Dimyristoylphosphatidylcholine
DPPC Dipalmitoylphosphatidylcholine
DSPC Distearoylphosphatidylcholine
POPC Palmitoyl-oleoylphosphatidylcholine
DOPC Dioleoylphosphatidylcholine
DOPE Dioleoylphosphatidylethanolamine
DMPE Dimyristoylphosphatidylethanolamine
DPPE Dipalmitoylphosphatidylethanolamine
CHEMS Cholesterolhemisuccinate
CHIM Cholesterol-(3-imidazol-1-yl propyl)carbamate
DDAB Dimethyldioctadecylammonium bromide
DOTAP (1,2-dioleoyloxypropyl)-N,N,N-trimethylammonium salt
DOPS Dioleoylphosphatidylserine
DOPG Dioleoylphosphatidylglycerol
Chol-SO$_4$ cholesterol sulfate
MoChol 4-(2-Aminoethyl)-Morpholino-Cholesterol-hemisuccinate:

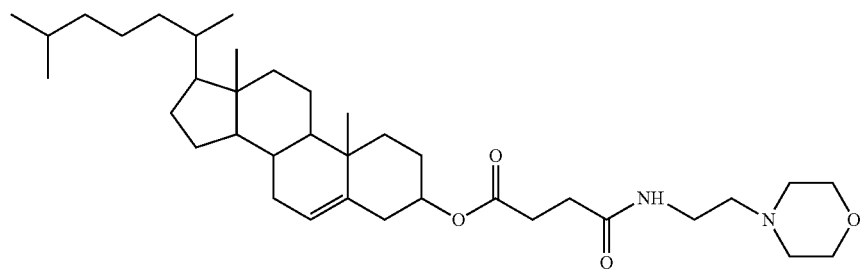 [SMILES: CC(C)CCCC(C)C1CCC2C3CC=C4CC(OC(=O)CCC(=O)NCCN5CCOCC5)CCC4(C)C3CCC12C]

HisChol Histaminyl-Cholesterolhemisuccinate:

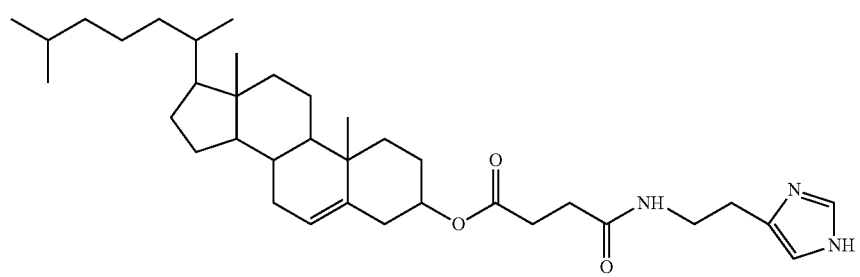 [SMILES: CC(C)CCCC(C)C1CCC2C3CC=C4CC(OC(=O)CCC(=O)NCCc5c[nH]cn5)CCC4(C)C3CCC12C]

DGSucc 1,2-Dipalmitoylglycerol-3-hemisuccinate (& Distearoyl-, dimyristoyl-Dioleoyl or palmitoyl-oleoyl-derivatives) (in the structure below the acyl chain is shown schematically)

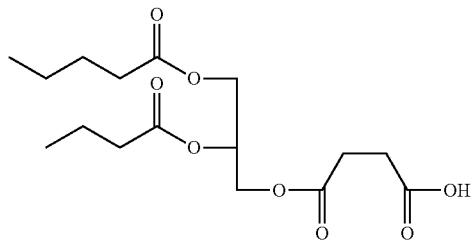 [SMILES: CCCCC(=O)OCC(COC(=O)CCC(=O)O)OC(=O)CCC]

It has been found that the ratio between the cationic and anionic lipids (the charge ratio) not only determines the isoelectric point, but may also affect the serum stability of the composition. Accordingly, said charge ratio may vary from 4:1 to 1:4, preferably between 3:1 and 1:3 (cation:anion).

In some embodiments of the invention, the cation may be present in excess over the anion. Preferably said charge ratio is between 3:1 and 2:1. The total amount of charged lipids may vary from 5 to 95 mol. % of the lipid mixture, preferably from 30 to 80 mol. %, and more preferably from 45 or 50 mol. % to 75 mol. %, with the remaining lipids being formed from the neutral phospholipids PC and PE.

Alternatively, the cation and anion may be present in substantially equal amounts. The total amount of charged lipids may vary from 5 to 75 mol. % of the lipid mixture, preferably from 20 to 65 mol. %, with the remaining lipids being formed from the neutral phospholipids PC and PE.

In another alternative, the anion may be present in excess over the cation. Said charge ratio may be between 1:3 and 1:2, preferably about 1:2 (cation:anion). The total amount of charged lipids may vary from 40 mol. % to 75 or 80 mol. % of the lipid mixture, preferably from 45 or 50 mol. % to 70 or 75 mol. %, with the remaining lipids being formed from the neutral phospholipids PC and PE.

A number of different combinations of cations and anions may be selected from the lists of suitable components given above. Advantageously, the invention may be practised using MoChol or CHIM as a chargeable cation and CHEMS, DMG-Succ or DOGSucc as a chargeable anion.

Presently preferred liposomes are made from a mixture of lipids comprising POPC and DOPE in a ratio between 1:1 and 1:4 and an amphoteric lipid pair selected from MoChol and CHEMS, MoChol and DMGSucc, MoChol and DOGSucc, CHIM and CHEMS, and CHIM and DMGSucc, in a ratio between 3:1 and 1:1, wherein the amount of charged lipids is between 30 and 80 mol. % of the lipid mixture.

Specific examples of such liposomes in accordance with the present invention include, but are not limited to:

| | |
|---|---|
| POPC/DOPE/MoChol/CHEMS | 6:24:53:17 |
| POPC/DOPE/MoChol/CHEMS | 6:24:47:23 |
| POPC/DOPE/MoChol/CHEMS | 15:45:20:20 |
| POPC/DOPE/MoChol/CHEMS | 10:30:30:30 |
| POPC/DOPE/MoChol/CHEMS | 24.5:35.5:20:20 |
| POPC/DOPE/MoChol/CHEMS | 16:24:30:30 |
| POPC/DOPE/MoChol/DMGSucc | 6:24:53:17 |
| POPC/DOPE/MoChol/DMGSucc | 6:24:47:23 |
| POPC/DOPE/MoChol/DMGSucc | 15:45:20:20 |
| POPC/DOPE/MoChol/DMGSucc | 10:30:30:30 |
| POPC/DOPE/MoChol/DMGSucc | 24.5:35.5:20:20 |
| POPC/DOPE/MoChol/DMGSucc | 16:24:30:30 |
| POPC/DOPE/MoChol/DOGSucc | 12.5:37.5:33:17 |
| POPC/DOPE/MoChol/DOGSucc | 7.5:22.5:47:23 |
| POPC/DOPE/CHIM/CHEMS | 12.5:37.5:33:17 |
| POPC/DOPE/CHIM/CHEMS | 7.5:22.5:47:23 |
| POPC/DOPE/CHIM/DMGSucc | 12.5:37.5:33:17 |
| POPC/DOPE/CHIM/DMGSucc | 7.5:22.5:47:23 |

Further presently preferred liposomes comprise a mixture of lipids comprising POPC and DOPE in a ratio between 1:1 and 1:4, DMGSucc or DOGSucc, and MoChol, wherein the molar amount of DMGSucc or DOGSucc exceeds the molar amount of MoChol and the amount of charged lipids is between 30 and 80 mol. %. Preferably, the charge ratio is between 1:2 and 1:3 and charged components constitute between 45 or 50 mol. % and 70 or 75 mol. % of the lipid mixture.

Specific examples of such further liposomes include, but are not limited to:

| | |
|---|---|
| POPC/DOPE/MoChol/DMGSucc | 6:24:23:47 |
| POPC/DOPE/MoChol/DMGSucc | 8:32:20:40 |
| POPC/DOPE/MoChol/DMGSucc | 10:40:17:33 |
| POPC/DOPE/MoChol/DMG Succ | 10:20:23:47 |
| POPC/DOPE/MoChol/DMGSucc | 13:27:20:40 |
| POPC/DOPE/MoChol/DMGSucc | 10:30:20:40 |
| POPC/DOPE/MoChol/DMGSucc | 17:33:17:33 |
| POPC/DOPE/MoChol/DOGSucc | 12.5:37.5:17:33 |

Without being limited to such use, the materials described in the present invention are well suited for use as carriers for nucleic acid-based drugs such as for example oligonucleotides and DNA plasmids. These drugs are classified into nucleic acids that encode one or more specific sequences for proteins, polypeptides or RNAs and into oligonucleotides that can specifically regulate protein expression levels or affect the protein structure through inter alia interference with splicing and artificial truncation.

In some embodiments of the present invention, therefore, the nucleic acid-based therapeutic may comprise a nucleic acid that is capable of being transcribed in a vertebrate cell into one or more RNAs, which RNAs may be mRNAs, shRNAs, miRNAs or ribozymes, wherein such mRNAs code for one or more proteins or polypeptides. Such nucleic acid therapeutics may be circular DNA plasmids, linear DNA constructs, like MIDGE vectors (Minimalistic Immunogenically Defined Gene Expression) as disclosed in WO 98/21322 or DE 19753182, or mRNAs ready for translation (e.g., EP 1392341).

In another embodiment of the invention, oligonucleotides may be used that can target existing intracellular nucleic acids or proteins. Said nucleic acids may code for a specific gene, such that said oligonucleotide is adapted to attenuate or modulate transcription, modify the processing of the transcript or otherwise interfere with the expression of the protein. The term "target nucleic acid" encompasses DNA encoding a specific gene, as well as all RNAs derived from such DNA, being pre-mRNA or mRNA. A specific hybridisation between the target nucleic acid and one or more oligonucleotides directed against such sequences may result in an inhibition or modulation of protein expression. To achieve such specific targeting, the oligonucleotide should suitably comprise a continuous stretch of nucleotides that is substantially complementary to the sequence of the target nucleic acid.

Oligonucleotides fulfilling the abovementioned criteria may be built with a number of different chemistries and topologies. Oligonucleotides may be single stranded or double stranded.

The mechanisms of action of oligonucleotides may vary and might comprise effects on inter alfa splicing, transcription, nuclear-cytoplasmic transport and translation.

In a preferred embodiment of the invention single stranded oligonucleotides may be used, including, but not limited to, DNA-based oligonucleotides, locked nucleic acids, 2'-modified oligonucleotides and others, commonly known as antisense oligonucleotides. Backbone or base or sugar modifications may include, but are not limited to, Phosphothioate DNA (PTO), 2'O-methyl RNA (2'Ome), 2' O-methoxyethyl-RNA (2'MOE), peptide nucleic acids (PNA), N3'-P5' phosphoamidates (NP), 2'fluoroarabino nucleic acids (FANA), locked nucleic acids (LNA), Morpholine phosphoamidate (Morpholino), Cyclohexene nucleic acid (CeNA), tricyclo-DNA (tcDNA) and others. Moreover, mixed chemistries are known in the art, being constructed from more than a single nucleotide species as copolymers, block-copolymers or gapmers or in other arrangements. In addition to the aforementioned oligonucleotides, protein expression can also be inhibited using double stranded RNA molecules containing complementary sequence motifs. Such RNA molecules are known as siRNA molecules in the art (e.g., WO 99/32619 or WO 02/055693). Again, various chemistries were adapted to this class of oligonucleotides. Also, DNA/RNA hybrid systems are known in the art.

In another embodiment of the present invention, decoy oligonucleotides can be used. These double stranded DNA molecules and chemical modifications thereof do not target nucleic acids but transcription factors. This means that decoy oligonucleotides bind sequence-specific DNA-binding proteins and interfere with the transcription (e.g. Cho-Chung, et al. in Curr. Opin. Mol. Ther., 1999).

In a further embodiment of the invention, oligonucleotides that may influence transcription by hybridizing under physiological conditions to the promoter region of a gene may be used. Again various chemistries may adapt to this class of oligonucleotides.

In a still further alternative of the invention, DNAzymes may be used. DNAzymes are single-stranded oligonucleotides and chemical modifications thereof with enzymatic activity. Typical DNAzymes, known as the "10-23" model, are capable of cleaving single stranded RNA at specific sites under physiological conditions. The 10-23 model of DNAzymes has a catalytic domain of 15 highly conserved deoxyribonucleotides, flanked by 2 substrate-recognition domains complementary to a target sequence on the RNA. Cleavage of the target mRNAs may result in their destruction and the DNAzymes recycle and cleave multiple substrates.

In yet another embodiment of the invention, ribozymes can be used. Ribozymes are single stranded oligoribonucleotides and chemical modifications thereof with enzymatic activity. They can be operationally divided into two components, a conserved stem-loop structure forming the catalytic core and flanking sequences which are reverse complementary to sequences surrounding the target site in a given RNA transcript. Flanking sequences may confer specificity and may generally constitute 14-16 nt in total, extending on both sides of the target site selected.

In a still further embodiment of the invention, aptamers may be used to target proteins. Aptamers are macromolecules composed of nucleic acids, such as RNA or DNA, and chemical modifications thereof that bind tightly to a specific molecular target and are typically 15-60 nt long. The chain of nucleotides may form intramolecular interactions that fold the molecule into a complex three-dimensional shape. The shape of the aptamer allows it to bind tightly against the surface of its target molecule including but not limited to acidic proteins, basic proteins, membrane proteins, transcription factors and enzymes. Binding of aptamer molecules may influence the function of a target molecule.

All of the above-mentioned oligonucleotides may vary in length between as little as 10, preferably 15 and even more preferably 18, and 50, preferably 30 and more preferably 25, nucleotides. The fit between the oligonucleotide and the target sequence is preferably perfect with each base of the oligonucleotide forming a base pair with its complementary base on the target nucleic acid over a continuous stretch of the abovementioned number of oligonucleotides. The pair of sequences may contain one or more mismatches within the said continuous stretch of base pairs, although this is less preferred. In general, the type and chemical composition of such nucleic acids is of little impact for the performance of the inventive liposomes as vehicles be it in vivo or in vitro, and the skilled artisan may find other types of oligonucleotides or nucleic acids suitable for combination with the inventive liposomes.

In a preferred embodiment of the invention however, oligonucleotides may used that are adapted to target a nucleic acid encoding the CD40 gene, its sense or antisense strand, any exons or introns or untranslated regions thereof, thereby to modulate expression of CD40 in mammalian cells.

In another preferred embodiment of the invention, said oligonucleotides may directed against any mRNA of CD40, wherein such mRNAs include pre-mRNA and their subsequently matured forms.

Protein expression can be specifically down-regulated using oligonucleotides such, for example, as antisense, locked nucleic acids (LNA), peptide nucleic acids (PNA), morpholino nucleic acids (Morpholinos) and small interfering RNAs (siRNA) of various chemistries.

CD40 was first described by Pauli, et al. 1984 (Cancer Immunol. Immunotherapy 17: 173-179). The protein is primarily expressed on dendritic cells, endothelial cells and B-cells and interacts with its ligand (CD40 ligand or CD154) on T-cells. The signalling between CD40 and CD154 is crucial for the development of a humoral immune response. Over-stimulation of the pathway may lead to a variety of immune-associated disorders, including graft rejection, graft-versus-host disease, multiple sclerosis, systemic lupus erythematosus, rheumatoid arthritis, asthma, inflammatory bowel disease, psoriasis and thyroiditis. CD40 over-expression might also be involved in tumour growth (Gruss, et al. 1997, Leuk. Lymphoma. 24(5-6): 393-422) and enhanced levels of a soluble form of CD40 were reported to be associated with Alzheimers disease (Mocali et al. 2004, Exp Gerontol. 39(10):1555-61. CD40 signals into the NF-κB pathway, consequently leading to activation of the transcription factor and the eventual release of cytokines such as IL-1, TNFα and IFNγ, which in turn activate other cells, thus promoting inflammation using a positive feedback mechanism.

Inhibition of the early events in the pathway described above has been proposed as an effective strategy to inhibit immune disorders or inflammation processes. Examples include the competitive binding of TNFα using antibodies, receptor blocking using antibodies against the TNFα-receptor and competitive inhibition of NF-κB binding. Since CD40 signals through its interaction with the trimeric ligand, CD154, inhibition of the signalling event with small molecule inhibitors is unlikely and therapeutic developments have therefore focused on the use of blocking antibodies. More specifically, the CD40/CD154 interaction may be blocked using antibodies targeted against one of the components, as described by Holstager, et al. 2000 (J. Biol. Chem. 275: 15392-15398) or Baccam & Bishop 1999 (Eur. J. Immunol. 29: 3855-3866). However, the CD40 antibodies under development give rise to side reactions, and there is therefore a need for alternative means to cut the inflammatory feedback loop at this point.

A number of oligonucleotide sequences targeted against CD40 mRNA have been validated in vitro so far. US 2004/0186071 and U.S. Pat. No. 6,197,584, both to Bennett, et al., for example, give a detailed description of such oligonucleotides based on antisense mechanisms. Pluvinet, et al. in Blood, 2004 first described the down-regulation of CD40 using siRNA against the human target. Further, WO 2004/090108 to Manoharan describes the applicability of novel oligonucleotides to inhibit the expression of CD40 protein. Indirect means to down-regulate the CD40 expression are described in DE 10049549 to Hecker and Wagner, using the inhibition of transcription factor IFR-1. Suitable specific nucleic acids for modulating the expression of CD40 are set forth in Example 11 below.

In a particular aspect of the present invention therefore there is provided a pharmaceutical composition comprising an oligonucleotide directed against CD40 as an active agent and an amphoteric liposome of the present invention as an excipient. Such formulations have been found to be therapeutically active in the treatment of inflammations and autoimmune disorders, and accordingly the invention further comprehends the use of the composition of the invention for the prevention or treatment of inflammations, immune or autoimmune disorders, including graft rejection, graft-versus-host disease, multiple sclerosis, systemic lupus erythematosus, rheumatoid arthritis, asthma, asthma bronchiale, inflammatory bowel disease, psoriasis, thyroiditis, Morbus Crohn, Colitis ulcerosa, COPD and atopic dermatitis.

The pharmaceutical composition of the present invention may also be used for topical treatments, for example the treatment of inflamed mucosa. In particular, the composition of the invention may be used for the treatment or prophylaxis of inflammatory bowel disease or graft rejection. The composition of the present invention may also be adapted for topical application to the skin or lungs.

Liposomes have been widely used to alter the pharmacokinetic and biodistribution profile of encapsulated drugs in vivo. The liposomes of the present invention, together with their cargo, may be cleared rapidly and to a great extent by the liver. However, the pharmacokinetic parameters as well as the biodistribution pattern may be controlled by adjusting the size of the liposomes and/or the lipid dose as illustrated in the examples below.

In some embodiments, the liposomes of the present invention may have a size greater than about 150 nm. Such liposomes may be administered at a low lipid dose. Said liposomes may be unilamellar, oligolamellar or multilamellar. Such a dosing scheme allows for effective and rapid targeting to the liver and avoids the accumulation of liposomes and drug in other organs, such as the spleen.

Alternatively, such liposomes having a size greater than about 150 nm may be administered at a high lipid dose, leading to saturation of the liver and an alteration of the biodistribution pattern to an accumulation of the liposomes in the spleen and more distal sites in the circulation, such as sites of infection or inflammation or tumours. These areas of the body have fenestrated or incomplete capillaries through which liposomes may be filtered out. Furthermore, it is known that the spleen and such other areas of infection or inflammation and many tumors often have high contents of macrophages which can remove the liposomes from the circulation.

Said pharmaceutical composition according to the present invention may be provided with a high lipid dose by different methods. In some embodiments, the drug/lipid ratio of the composition can be lowered to achieve the desired lipid concentration. Alternatively, the lipid concentration of the pharmaceutical composition may be controlled by adding empty liposomes of comparable composition and size to the drug loaded liposomes.

In some embodiments, the liposomes according to the present invention may have a size of less than about 150 nm. Said liposomes may be unilamellar, oligolamellar or multilamellar. The spleen acts as a filter which removes unwanted red blood cells and particles from the blood. Large liposomes are also retained by the reticular filter in the same way. However, small liposomes may escape and thus do not accumulate in spleen. Accordingly, liposomes according to the present invention, having a size of less than 150 nm may circumvent the spleen as an organ.

Such liposomes having a size of less than 150 nm may be administered at a low lipid dose in order to target liver cells. Such liposomes are particularly well adapted to penetrate fully the entire liver and to reach a substantial portion of the parenchymal cells of the liver such as hepatocytes.

Alternatively, said liposomes having a size of less than 150 nm may be administered at a high lipid dose to target more distal sites in the circulation, such as areas of infection or inflammation or solid tumours, and simultaneously to circumvent the spleen.

In general, the pharmacokinetic profile and the biodistribution of the liposomes of the present invention may depend upon many factors. Next to the lipid composition of the liposomes, the size and lipid dose determine the in vivo fate of the liposomes. The liposomes of the invention may be unilamellar, oligolamellar or multilamellar, irrespective of their size.

In some embodiments, the liposomes of the present invention may be used to target an inflamed lung by systemic administration to a human or non-human animal patient.

Starting from the data presented herein, those skilled in the art will be able to establish appropriate dosage regimens for other species, in particular for other mammals or humans. Specifically, whether a lipid dose in another species (e.g. human) is "low" or "high" can be determined by pharmacokinetic data. The pharmacokinetic of liposomes follows a two compartment model. As mentioned above, high lipid doses lead to a saturation of the liver and an alteration of the biodistribution pattern. This leads to enhanced Cmax values in the terminal part of the pharmacokinetic curve.

The pharmaceutical composition of the present invention may be formulated for use as a colloid in a suitable pharmacologically acceptable vehicle. Vehicles such as water, saline, phosphate buffered saline and the like are well known to those skilled in the art for this purpose.

In some embodiments, the composition of the present invention may be administered at a physiological pH of between about 7 and about 8. To this end, the composition comprising the active agent, excipient and vehicle may be formulated to have a pH in this range.

Methods for manufacturing liposomes are known to those skilled in the art. They include, but are not limited to, extrusion through membranes of defined pore size, injection of lipid solutions in ethanol into the water phase containing cargo or high pressure homogenisation.

Also, it is known in the art that nucleic acid therapeutics can be contacted with the lipids at neutral pH, resulting in volume inclusion of a certain percentage of the solution containing the nucleic acid. High concentrations of lipids ranging from 50 mM to 150 mM are preferred to achieve substantial encapsulation of the drug.

In contrast to such standard procedures, amphoteric liposomes offer the distinct advantage of binding nucleic acids at or below their isoelectric point, thereby concentrating the drug at the liposome surface. Such a process is described in WO 02/066012 in more detail. Upon elevating the pH of the liposomes to physiological pH (about pH 7.4) the negatively charged nucleic acids dissociate from the liposomal membrane. Irrespective of the actual production process, the non-encapsulated active drug can be removed from the liposomes after the initial production step, wherein liposomes are formed as tight containers. Again, the technical literature and the references included here describe such methodology in detail and suitable process steps may include, but are not limited to, size exclusion chromatography, sedimentation, dialysis, ultrafiltration, diafiltration and the like.

In some embodiments of the invention, more than 80 wt. % of the drug may be disposed inside said liposomes.

However, such removal of non-encapsulated material is not mandatory and in some embodiments the composition may comprises entrapped as well as free drug.

The particle size of the liposomes may be between 50 and 500 nm, preferably between 50 and 300 nm.

Following is a description by way of example only with reference to the accompanying drawings of embodiments of the present invention.

EXAMPLES

Example 1

Preparation of carboxyfluorescein (CF) Loaded Liposomes with the Amphoteric II Lipids MoChol and CHEMS Stock solutions of lipids in chloroform were mixed and finally evaporated in a round bottom flask to dryness under vacuum. Lipid films were hydrated with 100 mM CF in PBS pH 7.5. The resulting lipid concentration was 20 mM. The suspensions were hydrated for 45 minutes in a water bath at room temperature, sonicated for 5 minutes following by three freeze/thaw cycles at −70° C. After thawing the liposomal suspensions were extruded 15 times through polycarbonate membranes with a pore size of 100 nm. Non-encapsulated CF was removed by gel filtration, whereas the liposomes were diluted by a factor of three. Lipid recovery and concentration was analysed by organic phosphate assay. Particle size was measured by dynamic light scattering on a Malvern Zetasizer 3000 HSA.

TABLE 1

Variation of the ratio DOPE/POPC and the total amount of charged components

| Lipids | Composition |
|---|---|
| DOPE/MoChol/CHEMS | 60:20:20 |
| DOPE/MoChol/CHEMS | 50:20:30 |
| DOPE/MoChol/CHEMS | 40:30:30 |
| DOPE/MoChol/CHEMS | 20:40:40 |
| POPC/MoChol/CHEMS | 60:20:20 |
| POPC/MoChol/CHEMS | 40:30:30 |
| POPC/MoChol/CHEMS | 20:40:40 |
| POPC | 100 |
| POPC/DOPE | 20:80 |
| POPC/DOPE/MoChol/CHEMS | 10:50:20:20 |
| POPC/DOPE/MoChol/CHEMS | 7:35:30:30 |
| POPC/DOPE/MoChol/CHEMS | 3:17:40:40 |
| POPC/DOPE | 25:75 |
| POPC/DOPE/MoChol/CHEMS | 15:45:20:20 |
| POPC/DOPE/MoChol/CHEMS | 10:30:30:30 |
| POPC/DOPE/MoChol/CHEMS | 5:15:40:40 |
| POPC/DOPE | 40:60 |
| POPC/DOPE/MoChol/CHEMS | 24.5:35.5:20:20 |
| POPC/DOPE/MoChol/CHEMS | 16:24:30:30 |
| POPC/DOPE/MoChol/CHEMS | 8:12:40:40 |
| POPC/DOPE | 57:43 |
| POPC/DOPE/MoChol/CHEMS | 34:26:20:20 |
| POPC/DOPE/MoChol/CHEMS | 22.8:17.2:30:30 |
| POPC/DOPE/MoChol/CHEMS | 11.4:8.6:40:40 |

TABLE 2

Variation of the ratio MoChol/CHEMS

| Lipids | Composition |
|---|---|
| POPC/DOPE/MoChol/CHEMS | 6:24:53:17 |
| POPC/DOPE/MoChol/CHEMS | 6:24:47:23 |
| POPC/DOPE/MoChol/CHEMS | 6:24:35:35 |
| POPC/DOPE/MoChol/CHEMS | 6:24:23:47 |

TABLE 3

Variation of ratio DOPE/POPC and the total amount of charged components

| Lipids | Composition |
|---|---|
| POPC/DOPE/MoChol/CHEMS | 4:16:27:53 |
| POPC/DOPE/MoChol/CHEMS | 6:24:23:47 |
| POPC/DOPE/MoChol/CHEMS | 8:32:20:40 |
| POPC/DOPE/MoChol/CHEMS | 10:40:17:33 |
| POPC/DOPE/MoChol/CHEMS | 7:13:27:53 |
| POPC/DOPE/MoChol/CHEMS | 10:20:23:47 |
| POPC/DOPE/MoChol/CHEMS | 13:26:20:40 |
| POPC/DOPE/MoChol/CHEMS | 17:33:17:33 |

Example 2

Preparation of carboxyfluorescein (CF) Loaded Liposomes with the Amphoteric II Lipids MoChol and DMGSucc Liposomes were prepared as described in Example 1.

TABLE 4

Variation of the ratio DOPE/POPC and the total amount of charged components

| Lipids | Composition |
|---|---|
| POPC/DOPE/MoChol/DMGSucc | 15:45:20:20 |
| POPC/DOPE/MoChol/DMGSucc | 10:30:30:30 |
| POPC/DOPE/MoChol/DMGSucc | 5:15:40:40 |
| POPC/DOPE/MoChol/DMGSucc | 24.5:35.5:20:20 |
| POPC/DOPE/MoChol/DMGSucc | 16:24:30:30 |
| POPC/DOPE/MoChol/DMGSucc | 8:12:40:40 |
| POPC/DOPE/MoChol/DMGSucc | 34:26:20:20 |
| POPC/DOPE/MoChol/DMGSucc | 22.8:17.2:30:30 |
| POPC/DOPE/MoChol/DMGSucc | 11.4:8.6:40:40 |

TABLE 5

Variation of the ratio MoChol/DMGSucc

| Lipids | Composition |
|---|---|
| POPC/DOPE/MoChol/DMGSucc | 6:24:53:17 |
| POPC/DOPE/MoChol/DMGSucc | 6:24:47:23 |
| POPC/DOPE/MoChol/DMGSucc | 6:24:35:35 |
| POPC/DOPE/MoChol/DMGSucc | 6:24:23:47 |

TABLE 6

Variation of ratio DOPE/POPC and the total amount of charged components

| Lipids | Composition |
|---|---|
| POPC/DOPE/MoChol/DMGSucc | 4:16:27:53 |
| POPC/DOPE/MoChol/DMGSucc | 6:24:23:47 |
| POPC/DOPE/MoChol/DMGSucc | 8:32:20:40 |
| POPC/DOPE/MoChol/DMGSucc | 10:40:17:33 |
| POPC/DOPE/MoChol/DMGSucc | 7:13:27:53 |
| POPC/DOPE/MoChol/DMGSucc | 10:20:23:47 |
| POPC/DOPE/MoChol/DMGSucc | 13:26:20:40 |
| POPC/DOPE/MoChol/DMGSucc | 17:33:17:33 |

Example 3

Preparation of carboxyfluorescein (CF) Loaded Liposomes with the Amphoteric II Lipids MoChol and DOGSucc Liposomes were prepared as described in Example 1.

TABLE 7

Variation of the ratio MoChol/DOGSucc and the total amount of charged components

| Lipids | Composition | Serum Stability |
|---|---|---|
| POPC/DOPE/MoChol/DOGSucc | 12.5:37.5:17:33 | + |
| POPC/DOPE/MoChol/DOGSucc | 12.5:37.5:33:17 | + |
| POPC/DOPE/MoChol/DOGSucc | 7.5:22.5:23:47 | − |
| POPC/DOPE/MoChol/DOGSucc | 7.5:22.5:47:23 | + |

Example 4

Preparation of carboxyfluorescein (CF) Loaded Liposomes with the Amphoteric II Lipids CHIM and CHEMS Liposomes were prepared as described in Example 1.

TABLE 8

Variation of the ratio CHIM/CHEMS and the total amount of charged components

| Lipids | Composition | Serum Stability |
|---|---|---|
| POPC/DOPE/CHIM/CHEMS | 12.5:37.5:17:33 | − |
| POPC/DOPE/CHIM/CHEMS | 12.5:37.5:33:17 | + |
| POPC/DOPE/CHIM/CHEMS | 7.5:22.5:23:47 | − |
| POPC/DOPE/CHIM/CHEMS | 7.5:22.5:47:23 | + |

Example 5

Preparation of carboxyfluorescein (CF) Loaded Liposomes with the Amphoteric II Lipids CHIM and DMGSucc Liposomes were prepared as described in Example 1.

TABLE 9

Variation of the ratio CHIM/DMGSucc and the total amount of charged components

| Lipids | Composition | Serum Stability |
|---|---|---|
| POPC/DOPE/CHIM/DMGSucc | 12.5:37.5:17:33 | − |
| POPC/DOPE/CHIM/DMGSucc | 12.5:37.5:33:17 | + |
| POPC/DOPE/CHIM/DMGSucc | 7.5:22.5:23:47 | − |
| POPC/DOPE/CHIM/DMGSucc | 7.5:22.5:47:23 | + |

Example 6

Serum Stability Test of CF-Loaded Amphoteric Liposomes of Examples 1 and 2

Carboxyfluorescein (CF) was used as model drug to determine the serum stability of amphoteric liposomes. As well as oligonucleotides, CF is negatively charged.

25 μl of the CF-loaded liposomes were mixed with 100 μl pre-warmed full human serum or PBS, respectively and incubated at 37° C. At defined time points 5 μl sample was transferred into a 96-well microliter plate to 20 μl PBS, pH 7.5 or 20 μl 20% Triton X-100. Finally 275 μl PBS were added to each well and fluorescence intensity was measured at 475/530 nm.

The serum stability was observed over a period of 4 hours by determining the release of CF from the liposomes via the fluorescence measurement. The released amount of CF (in %) is measured at defined time points as well as after a treatment of the liposomes with a detergent (Triton X-100) to get a 100% release value.

Figure 2:
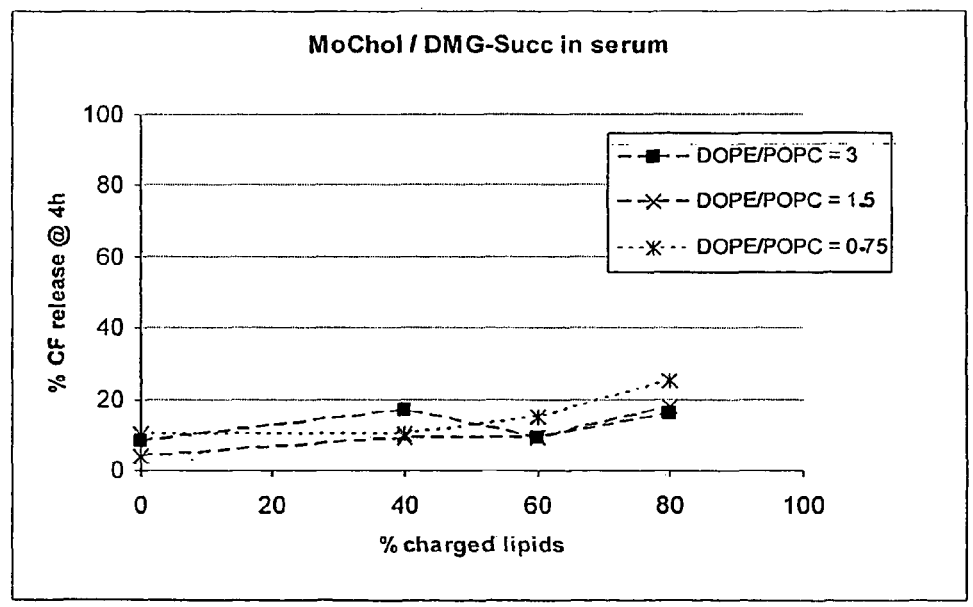
FIG. 2 is a graph of CF release from the MoChol/DMGSucc formulations of Table 4 (i.e., formulations comprising DOPE/POPC ratios of 3, 1.5, and 0.75) below after incubation in full human serum for 4 hours. CF release is expressed as % of the unquenched CF signal. The x-axis shows total amount of charged lipid at a 1:1 ratio between MoChol and DMGSucc.

Results:

Mixtures of POPC and DOPE are stable in serum. POPC itself does not form liposomes that withstand attack from serum. In addition, DOPE does not form liposomes at all. Quite surprisingly, mixtures from both components were found to be very stable and resistant against serum attack. In this example, DOPE/POPC ratios from 0.75 to 5 were found to form stable structures with a broad optimum between 1.5 and 5 (see also FIGS. 1 and 2).

Charged components and neutral lipids are independent variables. Serum sensitivity for a 1:1 ratio of both MoChol/CHEMS or MoChol/DMGSucc is low to very low and stable particles are formed over a wide range of mixtures. At least 60 or 70 mol. % of total charged components was required to affect significantly the bilayer stability.

Figure 3:
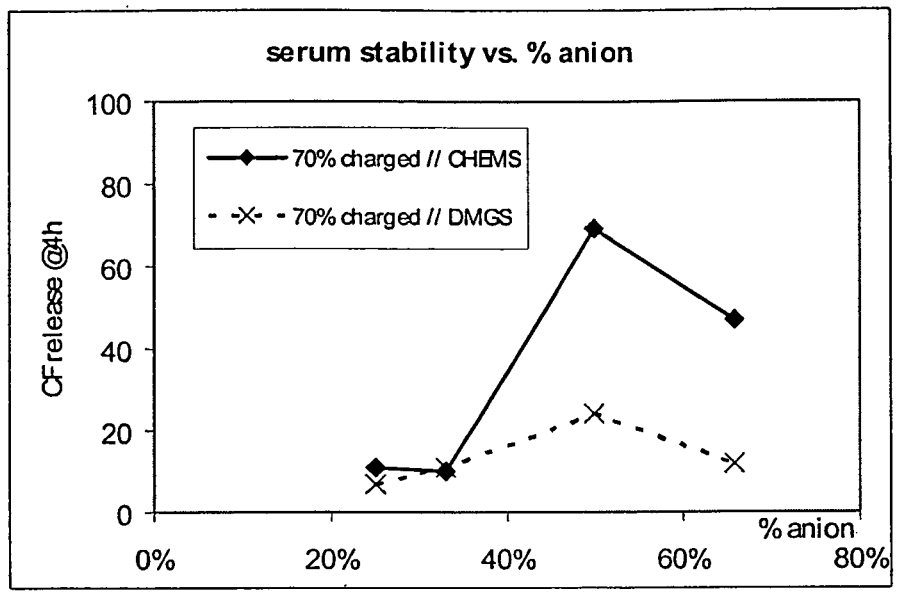
FIG. 3 is graph of CF release from liposomes containing MoChol/CHEMS or MoChol/DMGSucc after incubation in full human serum at 37° C. CF release is expressed as % of the unquenched CF signal. Excess cation stabilises the liposomes against serum attack. DMGSucc is notably more stable then the CHEMS counterpart.

The serum stability of lipid mixtures containing 70% of charged components (see Tables 2 and 5) is shown in FIG. 3. In general, an excess of MoChol has a stabilising effect.

Figure 4:
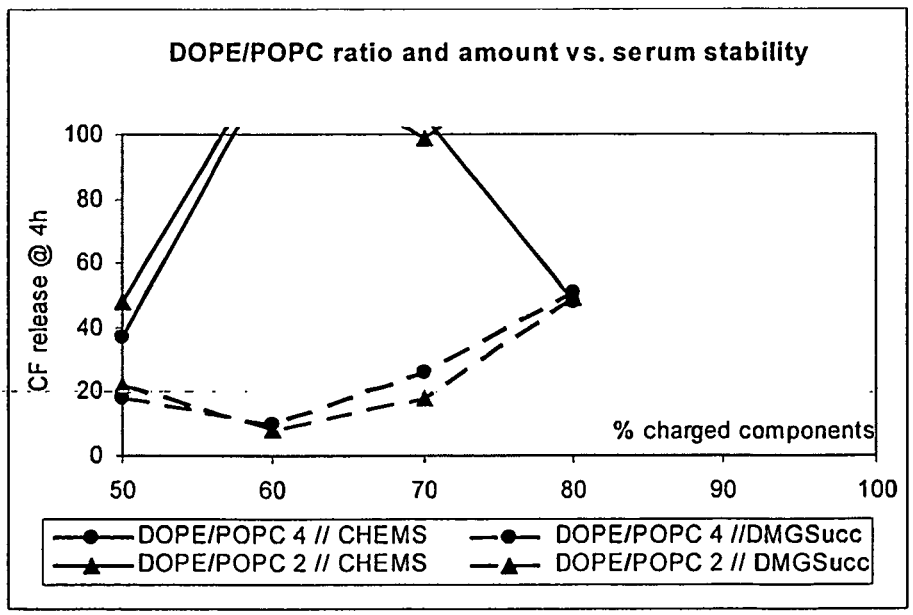
FIG. 4 is a graph of CF release from the MoChol/CHEMS and MoChol/DMGSucc formulations of Tables 3 and 6 below after incubation in full human serum at 37° C. The formulations have DOPE/POPC ratios of 2 and 4 and the ratio of cationic to anionic lipids is less than 1. Release is expressed as % of the unquenched CF signal.

The formulations of Tables 3 and 6 that were tested for serum stability have DOPE and POPC in a ratio of either 2:1 or 4:1. The total amount of the charged lipids was titrated from 80% down to 50%. The results are shown in FIG. 4.

Example 7

Biodistribution of Serum Stable Amphoteric Liposomes

Stock solutions of lipids (+/−1% 14C-DPPC) in chloroform were mixed and finally evaporated in a round bottom flask to dryness under vacuum. Lipid films were hydrated with 1.5 ml 3H-Inulin in PBS pH 7.5 or 5 ml PBS alone. The resulting lipid concentration was 100 mM. The suspensions were hydrated for 45 minutes in a water bath at room temperature, sonicated for 30 minutes following by three freeze/thaw cycles at −70° C. After thawing the liposomal suspensions were extruded 15 times through polycarbonate membranes with an appropriate pore size. Liposomes were separated from non-encapsulated 3H-Inulin by ultracentrifugation (twice).

Lipid recovery and concentration was analysed by organic phosphate assay and in case of radiolabelled particles, the encapsulation efficiency was measured by liquid scintillation. Particle size was measured by dynamic light scattering on a Malvern Zetasizer 3000 HSA. The resulting unlabelled and radiolabelled preparations were mixed up and diluted with PBS to the final lipid concentrations.

Formulations:

| Number | Formulation | Size [nm] | Lipid [mM] | 3H [kBq/ml] | 14C [kBq/ml] |
|---|---|---|---|---|---|
| LD-1 | POPC/DOPE/MoChol/CHEMS 15:45:20:20 | 229 | 12.3 | 332 | 52 |
| HD-2 | POPC/DOPE/MoChol/CHEMS 15:45:20:20 | 231 | 54.8 | 453 | 70 |
| LD-3 | POPC/DOPE/MoChol/CHEMS 15:45:20:20 | 148 | 10 | 173 | 53 |
| HD-4 | POPC/DOPE/MoChol/CHEMS 15:45:20:20 | 140 | 50 | 182 | 58 |

Biodistribution Study 39 male Wistar rats (Charles River) were divided into five groups and injected intravenously via the tail vein. At specific time points blood samples (for PK) and/or tissue samples (for BD) were collected and analysed by catalytic oxidation under high temperature. Percentage of carry over between samples was determined and included into the analysis of the data set.

| Study group | Formulation | Number | Animals |
|---|---|---|---|
| 1 | POPC/DOPE/MoChol/CHEMS 15:45:20:20 | LD-1 | 9 |
| 2 | POPC/DOPE/MoChol/CHEMS 15:45:20:20 | HD-2 | 9 |
| 3 | POPC/DOPE/MoChol/CHEMS 15:45:20:20 | LD-3 | 9 |
| 4 | POPC/DOPE/MoChol/CHEMS 15:45:20:20 | HD-4 | 9 |
| 5 | PBS | PBS | 3 |

Figure 5:
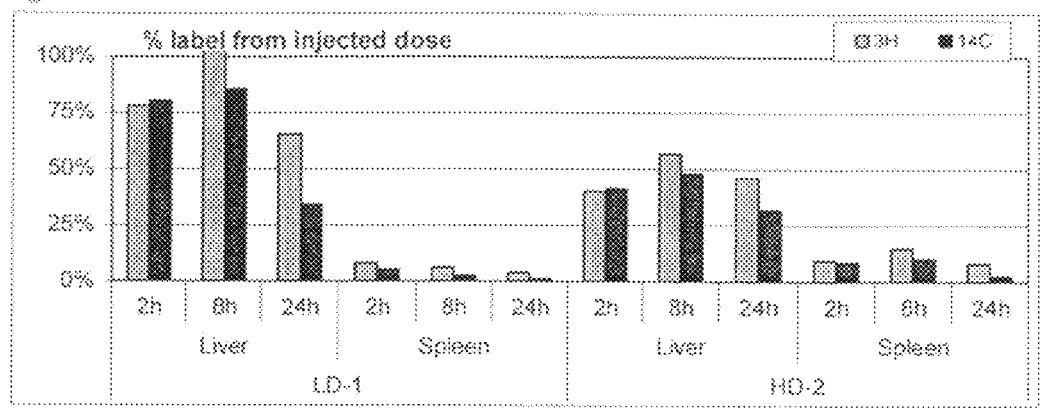
FIG. 5 is a bar chart showing the biodistribution of the formulation POPC/DOPE/MoChol/CHEMS 15:45:20:20 having a size >150 nm when administered at low and high lipid doses in rat liver and spleen (see Example 7 below).
Figure 6:
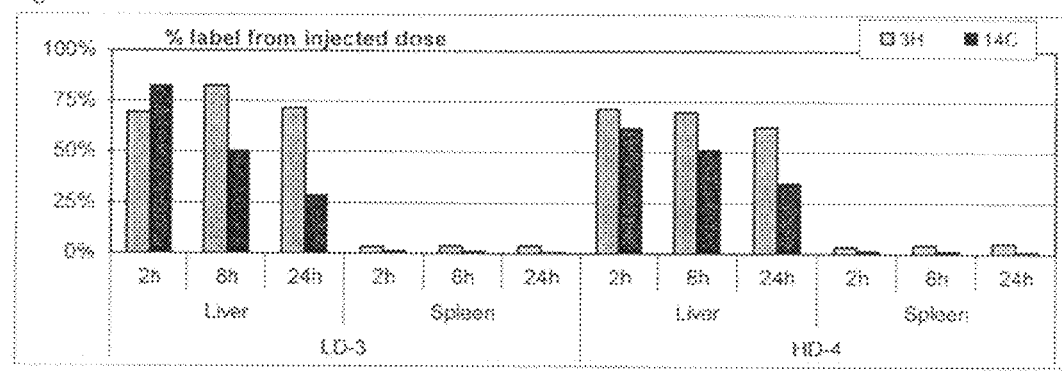
FIG. 6 is a bar chart showing the biodistribution of the formulation POPC/DOPE/MoChol/CHEMS 15:45:20:20 having a size <150 nm when administered at low and high lipid doses in rat liver and spleen (see Example 7 below).

The results of the biodistribution study are shown in FIGS. 5-6 wherein biodistribution of the different liposomal formulations in liver and spleen is shown. The accumulation of the liposomes in other organs did not exceed 5% and is therefore not shown. FIG. 5 clearly demonstrates that amphoteric liposomes of the present invention having a size >150 nm accumulate solely in the liver when administered in low lipid doses. In contrast, by administering the same liposomal formulation in a high lipid dose it could be shown that the biodistribution pattern is changed. Next to the liver the liposomes with a size >150 nm accumulate in spleen as well.

FIG. 6 shows the biodistribution of amphoteric liposomes of the present invention prepared in a size <150 nm. Whereas the biodistribution of these liposomes administered at low lipid dose does not differ from the liposomes with a size >150 nm, it can be demonstrated that an administration of the liposomes having a size <150 nm in high lipid dose does not lead to an accumulation in spleen.

Example 8

Biodistribution of Amphoteric Liposomes Encapsulating Cy5.5 Labelled CD40 Antisense in Collagen Induced Arthritic Mice Stock solutions of lipids in chloroform were mixed and finally evaporated in a round bottom flask to dryness under vacuum. Lipid film was hydrated with Cy5.5 labelled CD40 antisense in 10 mM NaAc, 50 mM NaCl, pH 4.5. The resulting lipid concentration was 20 mM. The suspensions were hydrated for 45 minutes in a water bath at 50° C., sonicated for 5 minutes following by a freeze/thaw cycle at −70° C. After thawing the liposomal suspensions were extruded 19 times through 200 nm polycarbonate membranes. After the extrusion process the pH of the liposomal suspension was shifted to pH 7.5 by adding 1/10 Vol. 1M HEPES, pH 8. Non-encapsulated Cy5.5 labelled CD40 antisense was removed by high speed sedimentation (twice) and discarding the supernatant.

Lipid recovery and concentration was analysed by organic phosphate assay. Encapsulation efficiency was measured by fluorescence spectroscopy. Particle size was measured by dynamic light scattering on a Malvern Zetasizer 3000 HSA.

Empty liposomes were produced by injecting 10 Vol-% of an ethanolic lipid solution (a mixture of 15 mol. % POPC, 45 mol. % DOPE, 20 mol. % MoChol and 20 mol. % CHEMS) into 10 mM NaAc 50 mM NaCl pH 4.5. The resulting lipid concentration was 2 mM. The pH of this solution was immediately shifted with 1/10 volume 1M Hepes pH 8. To concentrate the diluted liposomes the suspension was diafiltered.

| Formulation | Size [nm] | Lipid [mM] | Cargo | Encapsulation efficiency |
|---|---|---|---|---|
| POPC/DOPE/MoChol/CHEMS 15:45:20:20 | 192 | 19 | Cy5.5 OCD40-DN | 77% |
| POPC/DOPE/MoChol/CHEMS 15:45:20:20 | 104 | 195 | empty | — |

For the biodistribution study in mice the filled and empty liposomes were mixed as follows:

200 µl Cy5.5 liposomes and 41 µl empty liposomes

DBA/1 mice were immunized by subcutaneous injections of type II collagen (200 µg/mouse) emulsified in complete Freund's adjuvant. Mice were injected intravenously with the liposomal suspension (241 µl) at day 1 of arthritis induction (around day 21 after single immunization with collagen type II). Day one was defined as the day where the inflammation was obvious (clinical score after R. O. Williams of at least 2).

Figure 7:
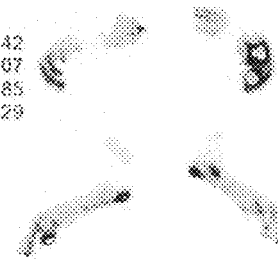
FIG. 7 is a set of photographs of the limbs of sacrificed collagen-induced arthritic mice obtained by NIR-imaging and showing the biodistribution of amphoteric liposomes encapsulating Cy5.5 labelled CD40 antisense (see Example 8 below).
Figure 7:
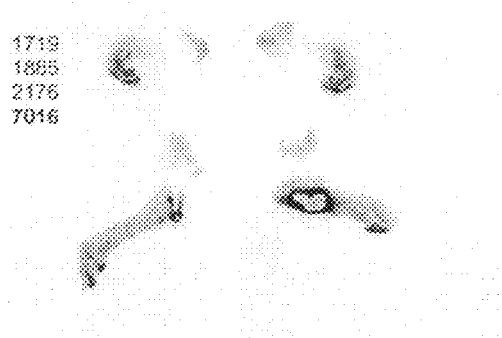
Figure 7:

Mice were sacrificed ten hours after the injection of the liposomal suspension. Organs and paws were removed and immediately frozen in liquid nitrogen. The biodistribution of the Cy5.5 labelled CD40 antisense encapsulated in the liposomes was assessed by NIR-Imaging and compared with tissue samples of untreated mice. Specific enrichment was found for inflamed paws in mice with active disease. More specifically, accumulation of the amphoteric liposomes coincides with the highly active sites of the disease on individual paws or even toes or fingers (see FIG. 7).

Example 9

Preparation of CD40-ODN-Containing Liposomes with the Advanced Loading Procedure Liposomes were produced by injecting 10 Vol-% of an ethanolic lipid solution (a mixture of 15 mol. % POPC, 45 mol. % DOPE, 20 mol. % MoChol and 20 mol. % CHEMS) into 10 mM NaAc 50 mM NaCl pH 4.5 containing 60 µg/ml of a 18 bp antisense against CD40.

The resulting lipid concentration was 2 mM. The pH of this solution was immediately shifted with 1/10 volume 1M Hepes pH 8. To concentrate the diluted liposomes the suspensions were sedimented for 2 h and 5 min at 65,000 rpm at 20° C. in a T865 rotor (Sorvall Ultra Pro 80). Afterwards the formulation was sterile filtered through 0.45 µm.

TABLE 9 example for Smarticles formulation which encapsulate CD40 ODN

| Lipid | Mol. % | size | Polydisp. Index |
|---|---|---|---|
| POPC/DOPE/MoChol/CHEMS | 15:45:20:20 | 178.5 | 0.317 |

The amount of encapsulated ODN was measured by checking the optical density (OD) by 260 nm. The following amount of ODN was encapsulated in the Smarticles formulation.

TABLE 10 encapsulated amount of ODN in the Smarticles formulation

| Lipid | Mol. % | µg ODN/µmol lipid | Encapsulation efficacy |
|---|---|---|---|
| POPC/DOPE/MoChol/CHEMS | 15:45:20:20 | 8.87 | 29.58% |

Example 10

Therapeutic Efficacy in Arthritis

DBA/1 mice were immunized by subcutaneous injections of type II collagen (200 µg/mouse) emulsified in complete Freund's adjuvant. Treatment with Smarticles or controls was initiated at day 1 of arthritis induction (around day 21 after single immunization with collagen type II) and repeated at day 3 and 5. Day one was defined as the day where the inflammation was obvious (clinical score after R. O. Williams of at least 2).

For the treatment studies the liposomal CD40-ODN was injected intravenously into the tail vein of rats with established inflammation. Each dosage contains 4 mg CD40-ODN per kg bodyweight (encapsulated CD40-ODN).

During the experiment the swelling of paws were observed and the clinical arthritis score were determined.

Figure 8:
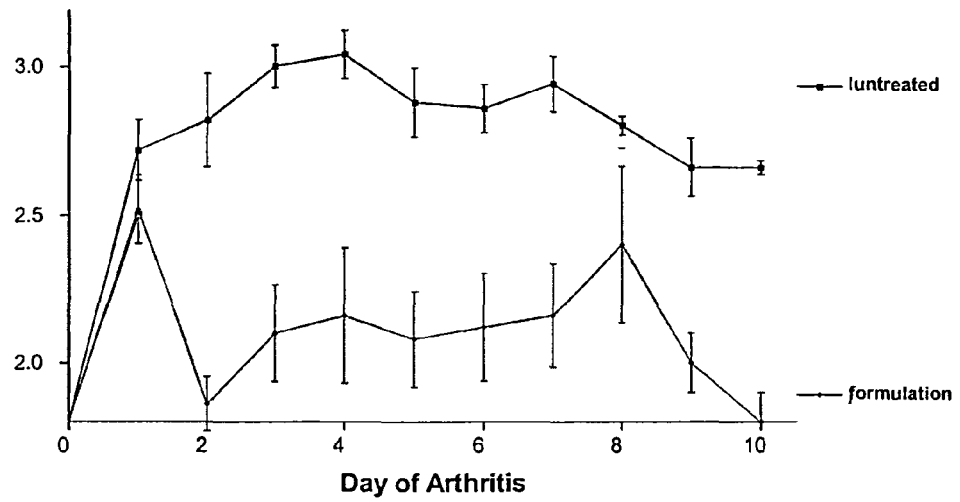
FIG. 8 is a graph showing the effect of treatment with amphoteric liposomes containing CD40 antisense on the paw swelling of inflamed mice.
Figure 9:
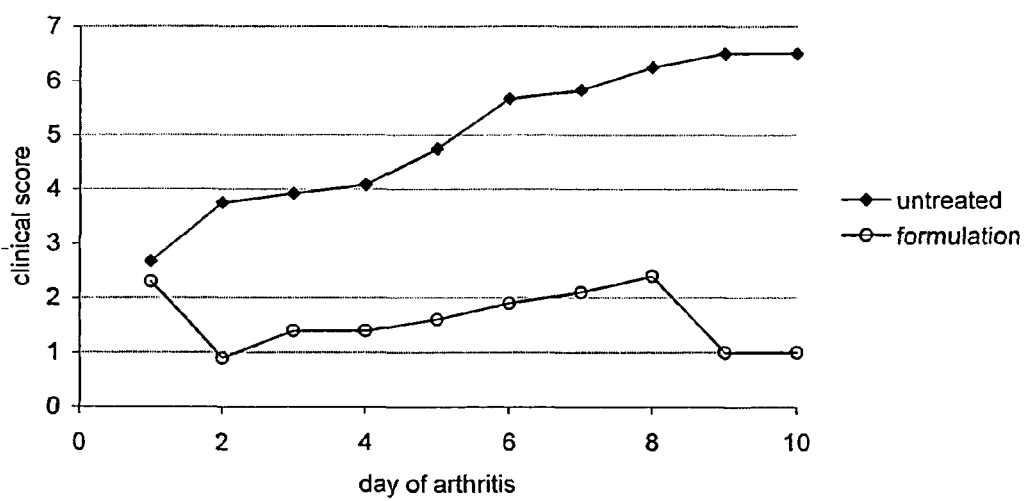
FIG. 9 is a graph of the assessed clinical score of mice treated with amphoteric liposomes containing CD40 antisense.

As evidenced by FIGS. 8 and 9, there was a significant reduction of the swelling of the paws after a treatment with CD40-ODN encapsulated in the amphoteric liposomes. Also the clinical score was significant reduced after treatment with CD40-ODN encapsulated in such liposomes.

Example 11

Materials

This example provides non-limiting examples of CD40 nucleotide sequences that may be targeted by oligonucleotides that modulate the expression of CD40 and that are suitable for use in the compositions in accordance with the present invention.

Human CD40 mRNA (GenBank accession no. X60592)

Human CD40 mRNA sequence for targeting in accordance with the present invention is presented in SEQ ID NO: 1. Related sequence information is found in published patent application number US 2004/0186071 (i.e., SEQ ID NO: 85) to Bennett, et al. and in U.S. Pat. No. 6,197,584 (i.e., SEQ ID NO: 85) to Bennett, et al. and in Pluvinet, et al., Blood, 2004, 104(12), 3642-3646, the contents of which are incorporated by reference herein.

```
(SEQ ID NO: 1):
  1 gcctcgctcg ggcgcccagt ggtcctgccg cctggtctca cctcgccatg gttcgtctgc 61 ctctgcagtg cgtcctctgg ggctgcttgc tgaccgctgt ccatccagaa ccacccactg 121 catgcagaga aaaacagtac ctaataaaca gtcagtgctg ttctttgtgc cagccaggac 181 agaaactggt gagtgactgc acagagttca ctgaaacgga atgccttcct tgcggtgaaa 241 gcgaattcct agacacctgg aacagagaga cacactgcca ccagcacaaa tactgcgacc 301 ccaacctagg gcttcgggtc cagcagaagg gcacctcaga aacagacacc atctgcacct 361 gtgaagaagg ctggcactgt acgagtgagg cctgtgagag ctgtgtcctg caccgctcat 421 gctcgcccgg ctttggggtc aagcagattg ctacaggggt ttctgatacc atctgcgagc 481 cctgcccagt cggcttcttc tccaatgtgt catctgcttt cgaaaaatgt caccctggta 541 caagctgtga gaccaaagac ctggttgtgc aacaggcagg cacaaacaag actgatgttg 601 tctgtggtcc ccaggatcgg ctgagagccc tggtggtgat ccccatcatc ttcgggatcc 661 tgtttgccat cctcttggtg ctggtcttta tcaaaaaggt ggccaagaag ccaaccaata 721 aggccccccca ccccaagcag gaaccccagg agatcaattt tcccgacgat cttcctggct 781 ccaacactgc tgctccagtg caggagactt tacatggatg ccaaccggtc acccaggagg 841 atggcaaaga gagtcgcatc tcagtgcagg agagacagtg aggctgcacc cacccaggag 901 tgtggccacg tgggcaaaca ggcagttggc cagagagcct ggtgctgctg ctgcaggggt 961 gcaggcagaa gcggggagct atgcccagtc agtgccagcc cctc
```

Mus Musculus CD40 mRNA

Murine CD40 mRNA sequence for targeting in accordance with the present invention is presented in SEQ ID NO: 2. Related sequence information is found in published patent application number US 2004/0186071 (i.e. SEQ ID NO: 132) to Bennett, et al., the contents of which are incorporated by reference herein.

(SEQ ID NO: 2):
```
gcctcctggc ccttcagctg tggtctttcc cgttttctga ctttgcggtg acactgggga  60
cttccttaga cctctctgga gacgctttcg gttctgcaga gattcccagg ggtattgtgg 120
gtggggtggg gtaacaatag tgtccctgtg gcgctcccag tccctatagt aatccttcac 180
cectctgcta tcttgcaatc aggagagtcc ttagccctgc tataggtggc ttttgaggtc 240
ctggatgcga ggaggggac tgggggtgg gtcgggtaat gtaagaaaag ggctccttt  300
gggaccctgg ctcctccagc caccttggtg cccatccctt aaactcttgg ggacaatcag 360
actcctggga aggtcctggg gaaatccctg ctcagtgact agccataggc ccaccgcgat 420
tggtgcccga agaccccgcc ctcttcctgg gcgggactcc tagcagggac tttggagtga 480
cttgtggctt cagcaggagc cctgtgattt ggctcttctg atctcgccct gcgatggtgt 540
ctttgcctcg gctgtgcgcg ctatgggct gcttgttgac agcggtgagt ggcttgtgtt 600
ctaacctcca agggagttag ggcttagaga gtgagagatg gaaagaggaa agaggagaca 660
agactttgga gatgagagat cttcctactg gaagcggcgg ttagtaggat gggcaagatc 720
tctcgcgtct tgacacacac acacacacac acaaatgagg tgggctgctc ctctttcctt 780
ccagaaggtc ggggttctgt tccacgaagc ccacagggaa ccttagggag ggcattcctc 840
cacagcggtg cctggacagc tttgtctgac ccaagccttg ctccggagct gactgcagag 900
actggaaagg gttagcagac aggaagcctg gctggggg                         938
```

Rat CD40 mRNA (GenBank Accession No. AF 241231)

Rat CD40 mRNA sequence for targeting in accordance with the present invention is presented in SEQ ID NO: 3. (See, Gao, Ph.D. thesis, Goettingen 2003).

(SEQ ID NO: 3):
```
  1 tgggacccct gtgatctggc tgctctgatc tcgctctgca atgctgcctt tgcctcagct
 61 gtgcgcgctc tggggctgct tgttgacagc ggtccatcta ggacagtgtg ttacgtgcag
121 tgacaaacag tacctccaag gtggcgagtg ctgcgatttg tgccagccgg gaaaccgact
181 agttagccac tgcacagctc ttgagaagac ccaatgccaa ccgtgcgact caggcgaatt
241 ctcagctcac tggaacaggg agatccgctg ccaccagcac cgacactgcg aactcaatca
301 agggcttcag gttaagaagg agggcaccgc ggtntcagac actgtttgta cctgcaagga
361 agggcagcac tgcgccagca aggagtgcga gacgtgcgct cagcacaggc cctgtggccc
421 tggctttgga gtcgtgcaga tggccactga gactactgat accgtctgcc aaccctgccc
481 ggtcggattc ttctccaatg ggtcatcact ttttgaaaag tgtcatccat ggacaagctg
541 tgaagat
```

Porcine CD40 cDNA

Porcine CD40 cDNA sequence for targeting in accordance with the present invention is presented in SEQ ID NO: 4. (FIG. 10). Related sequence information is found in Rushworth, et al., *Transplantation*, 2002, 73(4), 635-642, the contents of which are incorporated by reference herein.

In addition, the following provide non-limiting examples of anti-CD40 oligonucleotides, e.g., antisense CD40 nucleic acid sequences, that are suitable for use in the present invention:

Oligonucleotides Against Human CD40

Examples of human antisense CD40 oligonucleotides are presented below. Further sequence information is found in published patent application number US 2004/0186071 and U.S. Pat. No. 6,197,584 to Bennett, et al., the contents of which are provided by reference herein. The SEQ ID NOS. referred to by Bennett, et al. are provided to the right.

SEQ ID NO: 5  ccaggcggca ggaccact  Seq ID No: 1 of Bennett et al.
SEQ ID NO: 6  gaccaggcgg caggacca  Seq ID No.: 2 of Bennett et al.
SEQ ID NO: 7  aggtgagacc aggcggca  Seq ID No: 3 of Bennett et al.
SEQ ID NO: 8  gcagaggcag acgaacca  Seq ID No: 5 of Bennett et al.
SEQ ID NO: 9  gcaagcagcc ccagagga  Seq ID No: 6 of Bennett et al.
SEQ ID NO: 10 ggtcagcaag cagcccca  Seq ID No.: 7 of Bennett et al.
SEQ ID NO: 11 gacagcggtc agcaagca  Seq ID No: 8 of Bennett et al.
SEQ ID NO: 12 gatggacagc ggtcagca  Seq ID No: 9 of Bennett et al.
SEQ ID NO: 13 tctggatgga cagcggtc  Seq ID No: 10 of Bennett et al.
SEQ ID NO: 14 ggtggttctg atggaca   Seq ID No: 11 of Bennett et al.
SEQ ID NO: 15 gtgggtggtt ctggatgg  Seq ID No: 12 of Bennett et al.
SEQ ID NO: 16 gcagtgggtg gttctgga  Seq ID No: 13 of Bennett et al.
SEQ ID NO: 17 ctggcacaaa gaacagca  Seq ID No: 15 of Bennett et al.
SEQ ID NO: 18 gtgcagtcac tcaccagt  Seq ID No: 20 of Bennett et al.
SEQ ID NO: 19 attccgtttc agtgaact  Seq ID No: 23 of Bennett et al.
SEQ ID NO: 20 ttcaccgcaa ggaaggca  Seq ID No: 25 of Bennett et al.
SEQ ID NO: 21 ctctgttcca ggtgtcta  Seq ID No: 26 of Bennett et al.
SEQ ID NO: 22 ctggtggcag tgtgtctc  Seq ID No: 27 of Bennett et al.
SEQ ID NO: 23 ggtgcccttc tgctggac  Seq ID No: 31 of Bennett et al.
SEQ ID NO: 24 ctgaggtgcc cttctgct  Seq ID No: 32 of Bennett et al.
SEQ ID NO: 25 gtgtctgttt ctgaggtg  Seq ID No: 33 of Bennett et al.
SEQ ID NO: 26 acaggtgcag atggtgtc  Seq ID No: 35 of Bennett et al.
SEQ ID NO: 27 gtgccagcct tcttcaca  Seq ID No: 37 of Bennett et al.
SEQ ID NO: 28 tgcaggacac agctctca  Seq ID No: 40 of Bennett et al.
SEQ ID NO: 29 gagcggtgca ggacacag  Seq ID No: 41 of Bennett et al.
SEQ ID NO: 30 aatctgcttg accccaaa  Seq ID No: 43 of Bennett et al.
SEQ ID NO: 31 gctcgcagat ggtatcag  Seq ID No: 46 of Bennett et al.
SEQ ID NO: 32 gcagggctcg cagatggt  Seq ID No: 47 of Bennett et al.
SEQ ID NO: 33 gactgggcag ggctcgca  Seq ID No: 49 of Bennett et al.
SEQ ID NO: 34 gcagatgaca cattggag  Seq ID No: 52 of Bennett et al.
SEQ ID NO: 35 tcgaaagcag atgacaca  Seq ID No: 53 of Bennett et al.
SEQ ID NO: 36 gtccaagggt gacatttt  Seq ID No: 54 of Bennett et al.
SEQ ID NO: 37 caggtctttg gtctcaca  Seq ID No: 57 of Bennett et al.
SEQ ID NO: 38 ctgttgcaca accaggtc  Seq ID No: 58 of Bennett et al.
SEQ ID NO: 39 gtttgtgcct gcctgttg  Seq ID No: 59 of Bennett et al.
SEQ ID NO: 40 gtcttgtttg tgcctgcc  Seq ID No: 60 of Bennett et al.
SEQ ID NO: 41 caccaccagg gctctcag  Seq ID No: 64 of Bennett et al.
SEQ ID NO: 42 gggatcacca ccagggct  Seq ID No: 65 of Bennett et al.
SEQ ID NO: 43 gtcgggaaaa ttgatctc  Seq ID No: 71 of Bennett et al.
SEQ ID NO: 44 ggagccagga agatcgtc  Seq ID No: 73 of Bennett et al.
SEQ ID NO: 45 tggagccagg aagatcgt  Seq ID No: 74 of Bennett et al.

-continued

SEQ ID NO: 46 tggcatccat gtaaagtc Seq ID No: 77 of Bennett et al.

SEQ ID NO: 47 ggtgcagcct cactgtct Seq ID No: 81 of Bennett et al.

SEQ ID NO: 48 aactgcctgt ttgcccac Seq ID No: 82 of Bennett et al.

The following siRNA sequences are suitable for use in the present invention. (See, e.g., Pluvinet, et al., *Blood,* 2004, 104(12), 3642-3646), the contents of which are incorporated by reference herein.

```
(SEQ ID NO: 49):
5_-GCGAAUUCCUAGACACCUGUU-3_      (siRNA-2 of Pluvinet
3_-UUCGCUUAAGGAUCUGUGGAC-5_     et al.)

(SEQ ID NO: 50):
5_-CUGGUGAGUGACUGCACAGUU-3_      (siRNA-6 of Pluvinet
3_-UUGACCACUCACUGACGUGUC-5_     et al.)
```

-continued
```
(SEQ ID NO: 51):
5_-UACUGCGACCCCAACCUAGUU-3_      (siRNA-8 of Pluvinet
3_-UUAUGACGCUGGGGUUGGAUC-5_     et al.)
```

All siRNA contain a 2 nucleotide overhang at 3'ends.
Oligonucleotides Against Murine CD40
Examples of murine antisense CD40 oligonucleotides are presented below. Further sequence information is found in published patent application number US 2004/0186071 to Bennett, et al., the contents of which are hereby incorporated by reference herein. The SEQ ID NOS. referred to by Bennett, et al. are provided to the right.
Murine

| | | |
|---|---|---|
| SEQ ID NO: 52 | agacaccatc gcag | Seq. ID No. 116 of Bennett et al. |
| SEQ ID NO: 53 | gcgagatcag aagag | Seq. ID No. 117 of Bennett et al. |
| SEQ ID NO: 54 | cgctgtcaac aagca | Seq. ID No. 118 of Bennett et al. |
| SEQ ID NO: 55 | ctgccctaga tggac | Seq. ID No. 119 of Bennett et al. |
| SEQ ID NO: 56 | ctggctggca caaat | Seq. ID No. 120 of Bennett et al. |
| SEQ ID NO: 57 | cttgtccagg gataa | Seq. ID No. 123 of Bennett et al. |
| SEQ ID NO: 58 | cacagatgac attag | Seq. ID No. 124 of Bennett et al. |
| SEQ ID NO: 59 | tgatatagag aaaca | Seq. ID No. 125 of Bennett et al. |
| SEQ ID NO: 60 | ctcattatcc tttgg | Seq. ID No. 127 of Bennett et al. |
| SEQ ID NO: 61 | ggttcagacc agg | Seq. ID No. 128 of Bennett et al. |
| SEQ ID NO: 62 | tttatttagc cagta | Seq. ID No. 130 of Bennett et al. |
| SEQ ID NO: 63 | agccccacgc actgg | Seq. ID No. 131 of Bennett et al. |
| SEQ ID NO: 64 | tctcactcct atcccagt | Seq. ID No. 134 of Bennett et al. |
| SEQ ID NO: 65 | attagtctga ctcgt | Seq. ID No. 138 of Bennett et al. |
| SEQ ID NO: 66 | acattagtct gactc | Seq. ID No. 139 of Bennett et al. |
| SEQ ID NO: 67 | cagatgacat tagtc | Seq. ID No. 142 of Bennett et al. |
| SEQ ID NO: 68 | ctggactcac cacag | Seq. ID No. 143 of Bennett et al. |
| SEQ ID NO: 69 | ggactcacca cagat | Seq. ID No. 144 of Bennett et al. |
| SEQ ID NO: 70 | actcaccaca gatga | Seq. ID No. 145 of Bennett et al. |
| SEQ ID NO: 71 | tcaccacaga tgaca | Seq. ID No. 146 of Bennett et al. |
| SEQ ID NO: 72 | accacagatg acatt | Seq. ID No. 147 of Bennett et al. |
| SEQ ID NO: 73 | agatgacatt ag | Seq. ID No. 153 of Bennett et al. |
| SEQ ID NO: 74 | cagatgacat tag | Seq. ID No. 154 of Bennett et al. |
| SEQ ID NO: 75 | acagatgaca ttag | Seq. ID No. 155 of Bennett et al. |
| SEQ ID NO: 76 | ccacagatga cattag | Seq. ID No. 156 of Bennett et al. |
| SEQ ID NO: 77 | accacagatg acattag | Seq. ID No. 157 of Bennett et al. |
| SEQ ID NO: 78 | caccacagat gacattag | Seq. ID No. 158 of Bennett et al. |

-continued

SEQ ID NO: 79 tcaccacaga tgacattag Seq. ID No. 159 of Bennett et al.

SEQ ID NO: 80 ctcaccacag atgacattag Seq. ID No. 160 of Bennett et al.

Oligonucleotides Against Rat CD40

Examples of rat antisense CD40 oligonucleotides are presented below. (See, Gao, Ph.D. thesis, 2003, University of Gottingen, Germany).

SEQ ID NO: 81     accgctgtc aacaagcagc (rAS2 of Gao)

SEQ ID NO: 82     tcctagatggaccgctgt (rAS3 of Gao)

SEQ ID NO: 83     taacacactgtcctag (rAS4 of Gao)

Oligonucleotides Against Porcine CD40

Examples of porcine antisense CD40 oligonucleotides are presented below. See, Rushworth, et al., Transplantation, 2002, 73(4), 635-642, the contents of which are incorporated by reference herein.

SEQ ID NO: 84     gctgatgacagtgtttct
                      Aso3 of Rushworth et al.)

SEQ ID NO: 85     gcctcactctcgctcctg
                      (Aso8 of Rushworth et al.)

SEQ ID NO: 86     ggactgtatctggactgc
                      (Aso9 of Rushworth et al.)

SEQ ID NO: 87     gtggacagtcatgtatat
                      (Aso10 of Rushworth et al.)

The present invention therefore provides formulations of amphoteric liposomes that exhibit improved stability upon contact with mammalian serum, releasing less or no encapsulated drugs. Such liposomal formulations may be useful in the delivery of drugs after a systemic administration into the blood stream. The invention especially suits the delivery of oligonucleotides, a new class of drugs that is currently under development, and DNA plasmids, without being limited to such uses. The majority of such compounds have an intracellular site of action. Carrier systems are used to overcome the poor uptake of such substances and are sometimes an indispensable prerequisite.

Other embodiments and uses of the invention will be apparent to those skilled in the art from consideration of the specification and practice of the invention disclosed herein. All patents, patent applications, and other references noted herein for whatever reason are specifically incorporated by reference. The specification and examples should be considered exemplary only with the true scope and spirit of the invention indicated by the following claims.

What is claimed is:

1. An amphoteric liposome comprising POPC, MoChol, CHEMS, and DOPE, wherein the amphoteric liposome retains at least 60% of an encapsulated active agent after 4 hours exposure to human serum, wherein MoChol and CHEMS combined comprise 50 to 80 mol % of the amphoteric liposome, wherein POPC and DOPE combined comprise 20 to 50 mol % of the amphoteric liposome, wherein POPC, MoChol, CHEMS, and DOPE combined comprise substantially 100 mol % of the amphoteric liposome, wherein the ratio of DOPE to POPC is from 2 to 4, and wherein the ratio of CHEMS to MoChol is from 0.3 to 0.75.

2. The amphoteric liposome of claim 1, wherein the liposome consists of a formulation selected from:
POPC/DOPE/MoChol/CHEMS 6:24:47:23 (mol. %)
POPC/DOPE/MoChol/CHEMS 10:30:30:30 (mol. %).

3. The amphoteric liposome of claim 1, wherein the liposome has a size of from 50 to 500 nm.

4. The amphoteric liposome of claim 1, wherein the liposome encapsulates at least one active agent.

5. The amphoteric liposome of claim 4, wherein the active agent comprises a nucleic acid.

6. The amphoteric liposome of claim 4, wherein the active agent is a circular DNA plasmid, a linear DNA construct, an antisense oligonucleotide, a decoy oligonucleotide, an agent influencing transcription, an agent influencing splicing, a ribozyme, a DNAzyme, or an aptamer.

7. The amphoteric liposome of claim 4, wherein the active agent is an RNA, an siRNA, an mRNA, an shRNA, or an miRNA.

8. The amphoteric liposome of claim 4, wherein the active agent comprises one or more modified nucleosides selected from locked nucleic acids (LNA), peptide nucleic acids (PNA), 2'O-methyl RNA (2'Ome), or 2'O-methoxyethyl RNA (2'MOE) in their phosphate or phosphothioate forms.

9. The amphoteric liposome of claim 4, wherein the active agent modulates expression of CD40 in mammalian cells.

10. A pharmaceutical composition comprising an effective amount of the active agent-loaded amphoteric liposome of claim 4.

11. A method for treating an inflammatory, immune, or autoimmune disorder in a human in need thereof, the method comprising administering to the human a pharmaceutical composition according to claim 10.

12. The method of claim 11, wherein the inflammatory, immune, or autoimmune disorder is graft rejection, graft-versus-host disease, diabetes type I, multiple sclerosis, systemic lupus erythematosous, rheumatoid arthritis, asthma, inflammatory bowel disease, Crohn's disease, ulcerative colitis, psoriasis, thyroiditis, infection, or a solid tumor.

13. The method of claim 11, wherein the pharmaceutical composition is administered systemically.

14. The method of claim 11, wherein the pharmaceutical composition is administered locally.

* * * * *